United States Patent [19]

Corey

[11] Patent Number: 4,810,636

[45] Date of Patent: Mar. 7, 1989

[54] CHROMOGENIC ACRIDINONE ENZYME SUBSTRATES

[75] Inventor: Paul F. Corey, Elkhart, Ind.

[73] Assignee: Miles Inc., Elkhart, Ind.

[21] Appl. No.: 123,537

[22] Filed: Nov. 20, 1987

Related U.S. Application Data

[63] Continuation-in-part of Ser. No. 939,855, Dec. 9, 1986, abandoned.

[51] Int. Cl.[4] .................. C12Q 1/54; C12Q 1/38; C07D 211/00; C07D 219/00
[52] U.S. Cl. ........................................ 435/14; 435/18; 435/19; 435/21; 435/22; 435/23; 435/25; 435/805; 546/15; 546/18; 546/102; 546/103
[58] Field of Search ............... 546/15, 18, 102, 103; 435/14, 18, 19, 21, 22, 23, 25, 805; 422/56

[56] References Cited

U.S. PATENT DOCUMENTS

| 4,279,992 | 7/1981 | Boguslaski et al. | 435/7 |
|---|---|---|---|
| 4,649,108 | 5/1987 | Blair | 435/22 |
| 4,657,855 | 4/1987 | Corey et al. | 435/19 |

FOREIGN PATENT DOCUMENTS 0180961  5/1986  European Pat. Off. ............. 435/14

OTHER PUBLICATIONS

BMBiochemia, vol. 2, No. 6, (1985), p. 8, "New Chromogenic and Fluorogenic Substrates for β-Galactosidase".
Hill et al., J. Chem. Soc., (1970), pp. 2462–2466.
Tietz (ed), Fundamentals of Clinical Chemistry, 1976, p. 411.

*Primary Examiner*—Robert J. Warden
*Assistant Examiner*—Carol A. Spiegel
*Attorney, Agent, or Firm*—Daniel W. Collins

[57] ABSTRACT

Chromogenic acridinone enzyme substrate compounds comprising 7-hydroxy-9H-acridin-2-one chromogens derivatized at the 7-hydroxy-position with an enzymatically-cleavable group and disubstituted at the 9-position with alkyl or aryl groups, which can be the same or different, preferably lower alkyl or phenyl, respectively, or together form a cyclohexa-2,5-diene-4-one residue or a 4-hydroxycycloxhexyl residue, and 7-hydroxy-1,3-dihalo-9,9-dimethyl-acridin-2-one intermediates useful for the preparation of the novel chromogenic acridinone enzyme substrate compounds and methods therefor. The enzymatically-cleavable group is a radical of a compound Y-OH comprising an enzyme-specific moiety which is capable of being cleaved by a specific enzyme wherein a deprotonated form of the chromogen is liberated having an absorbance maximum in basic solution which is substantially greater than the absorbance maximum of the chromogenic acridinone enzyme substrate compound to provide a distinct change in absorbance which can be accurately measured and correlated to the amount of enzyme present in a liquid test sample.

68 Claims, 4 Drawing Sheets

(28)    (29)    (i)

(27)    (j)

(30)

CHROMOGENIC ACRIDINONE ENZYME SUBSTRATES

This is a continuation-in-part of copending application U.S. Ser. No. 939,855, filed Dec. 9, 1986, now abandoned.

BACKGROUND OF THE INVENTION

The present invention relates to chromogenic compounds which are useful as optical indicator compounds in analytical test systems. In particular, the present invention relates to novel chromogenic enzyme substrate compounds and their use in analytical test systems for the detection of enzymes in a liquid test sample.

The determination of enzymes is important in a variety of fields such as biochemical research, environmental and industrial testing, and medical diagnostics. The quantitation of enzyme levels in body fluids such as serum and plasma provides very useful information to the physician in diagnosing diseased states and their treatment. In addition to being analytes of interest in biological fluids, enzymes can also serve as detection reagents in a variety of analytical systems such as immunoassays and nucleic acid hybridization techniques. In such systems, enzymes are useful directly or indirectly as labels to monitor the extent of antigen-antibody binding or nucleic acid hybridization that occurs.

Accordingly, the desire to detect enzyme analyte and to use enzyme labels as a diagnostic tool in various analytical test systems has given rise to the development of optical indicator compounds for use in the detection and measurement of the activity of such enzymes. Typically, such known optical indicator compounds comprise a detectable chemical group, such as a fluorogen or a chromogen, which has been derivatized with an enzyme cleavable substrate group specific for the enzyme of interest. Such optical indicator compounds exhibit an optical signal which is different from the optical signal which is provided by the cleaved native form of the fluorogen or chromogen. In principle, the enzyme cleaves the indicator compound to liberate the fluorogen or chromogen in the form of a distinctly fluorescent or colored product to provide a change in fluorescence or color which is proportional to the amount of enzyme present which, in turn, can be correlated to the amount of analyte present in a liquid test sample.

In particular, the detection and/or determination of hydrolases, i.e., enzymes which catalyse hydrolysis reactions of esters, glycosidic bonds, peptide bonds, other carbon-nitrogen bonds, and acid anhydrides [see Lehninger, *Biochemistry* (Worth Publishers, Inc., New York, N.Y.,1970) p. 148], is of interest in the diagnosis and monitoring of various diseases such as, for example, the determination of amylase and lipase in the diagnosis of pancreatic dysfunction [see, Kaplan and Pesce, *Clinical Chemistry—Theory, Analysis and Correlation* (C. V. Mosby Co., St. Louis, Mo., 1984) Chapter 56], determination of N-acetylglucosaminidase (NAG) as an indicator of renal disease [see Price *Curr. Probl. Clin. Biochem.* 9, 150 (1979)] and detection of esterase as an indicator for leukocytes [see Skjold, *Clin. Chem.* 31, 993 (1985)]. Further to their value in disease monitoring, hydrolases in recent years have gained importance in the diagnostic as well as in the biotechnology areas. For example alkaline phosphatase and, preferably, β-D-galactosidase have found increasing use as indicator enzymes for enzyme immunoassays [see *Annals of Clinical Biochemistry* 16, 221–40 (1979)].

Accordingly, the use of enzymes such as glycosidases, particularly β-D-galactosidase, as indicator enzyme labels in analytical test systems has given rise to the development of substrate glycosides such as phenyl-β-D-galactoside, o-nitrophenyl-β-D-galactoside and p-nitrophenyl-β-D-galactoside [see *Biochem. Z.,* Vol. 333, p. 209 (1960)] which are hydrolysed by β-D-galactosidase to liberate the phenols which are determined photometrically in the ultraviolet range, or the nitrophenols which are determined in the shortwave visible range, respectively. European Patent Application No. 156,347 describes glycosides of resorufin derivatives which are specific for and cleaved by the particular glycosidase of interest to liberate the resorufin derivative which can be determined photometrically in the visible range or readily excited to fluorescence. Similarly, U.S. Pat. No. 3,950,322 describes an N-acylneuraminic acid derivatized with a fluorogen such as 4-methylumbelliferone, fluorescein, methylfluorescein, resorufin, or umbelliferone for the detection of neuraminidase where the fluorogenic substrate glycoside is similarly acted upon by the enzyme to liberate the fluorogen.

The use of β-D-galactosides has also been described in conjunction with histochemical investigations, such as the napthyl-β-D-galactosides described in *Histochemie,* Vol. 35, p. 199 and Vol. 37, p. 89 (1973), and the 6-bromo-α-napthyl derivatives thereof described in *J. Biol. Chem.,* Vol. 195, p. 239 (1952). According to such test systems, the napthols which are liberated upon the interaction of the galactoside with the enzyme are reacted with various diazonium salts to yield the respective azo-dyes which can then be visualized.

Various acridine compounds have been described as acridine dyes for use as indicator compounds in assays for the detection of hydrogen peroxide (European Patent Publication Nos. EP 38,205; 45,220; and 124,287), and as multiple fluorophore labels which induce self-quenching and which are enzymatically lysed to fluorescence (Canadian Patent No. 1,124,643). Acridine orange has also been described for use as a fluorescent biochemical stain (U.S. Pat. Nos. 3,793,131; 4,190,328; 4,257,775; and 4,345,027).

Although such known optical indicator compounds are useful for the detection of enzyme analytes and labels in an analytical test system, a number of problems nevertheless exist which effect assay sensitivity and accuracy such as low extinction coefficients, poor water solubility, absorbance maxima which interfere with various pigments and other constituents commonly present in biological fluids, and color shifts between the optical indicator compound and the liberated chromogen or fluorogen which are difficult to measure without the use of complicated instruments.

Accordingly, it is an object of the present invention to provide chromogenic enzyme substrate compounds which can be employed as optical indicator compounds in analytical test systems for the accurate and sensitive determination of enzymes in a liquid test sample.

Further, it is an object of the present invention to provide chromogenic enzyme substrate compounds which can be incorporated into the solid, porous matrix of an analytical test device as optical indicator compounds for the measurement of enzymes incorporated therein or in a liquid test sample applied hhereto.

SUMMARY OF THE INVENTION

The present invention provides novel chromogenic acridinone enzyme substrate compounds of the formula:

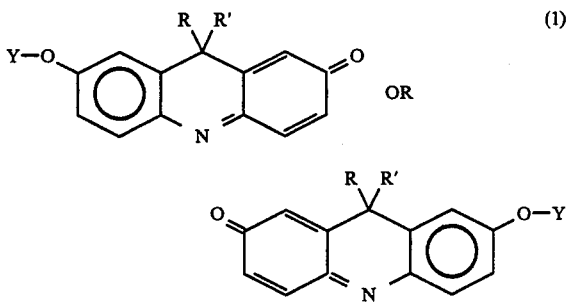

where Y represents an enzymatically-cleavable group which is selected to confer specificity to a specific corresponding enzyme, and R and R', which can be the same or different, are alkyl or aryl, preferably lower alkyl or phenyl, respectively, or together form a cyclohexa-2,5-diene-4-one residue or a 4-hydroxycyclohexyl residue. The enzymatically-cleavable group Y is a radical of a compound Y—OH comprising an enzyme-specific moiety which can be selected to confer specificity to any one of a wide variety of enzymes and includes, but is not necessarily limited to, enzyme-specific moieties such as sugars and derivatives thereof, acyl groups including aliphatic and aromatic carboxylic acids, amino acids and peptides, and inorganic acids such as phosphoric and sulfuric acids and the like.

The present invention derives its principal advantages from the use of 7-hydroxy-9H-acridin-2-one chromogens as intermediates which are derivatized with an appropriate enzymatically-cleavable group Y. In particular, when the enzymatically-cleavable group Y is cleaved by a specific enzyme therefor in a basic solution, preferably from between about pH 7.0 to pH 10.0, a deprotonated form of the chromogen is liberated having an absorbance maximum which is substantially greater than the absorbance maximum of the chromogenic enzyme substrate compound of the present invention whereby a distinct change in absorbance therebetween is provided. The distinct change in absorbance provides a readily observable and detectable optical signal which can be accurately measured and correlated to the amount of enzyme present in a liquid test sample.

The present invention further provides novel 7-hydroxy-1,3-dihalo-9,9-dimethyl-9H-acridin-2-one chromogen intermediates which are particularly useful for preparation of the chromogenic acridinone enzyme substrate compounds of the present invention and methods of preparation thereof.

DESCRIPTION OF THE PREFERRED EMBODIMENTS

Figure 1:
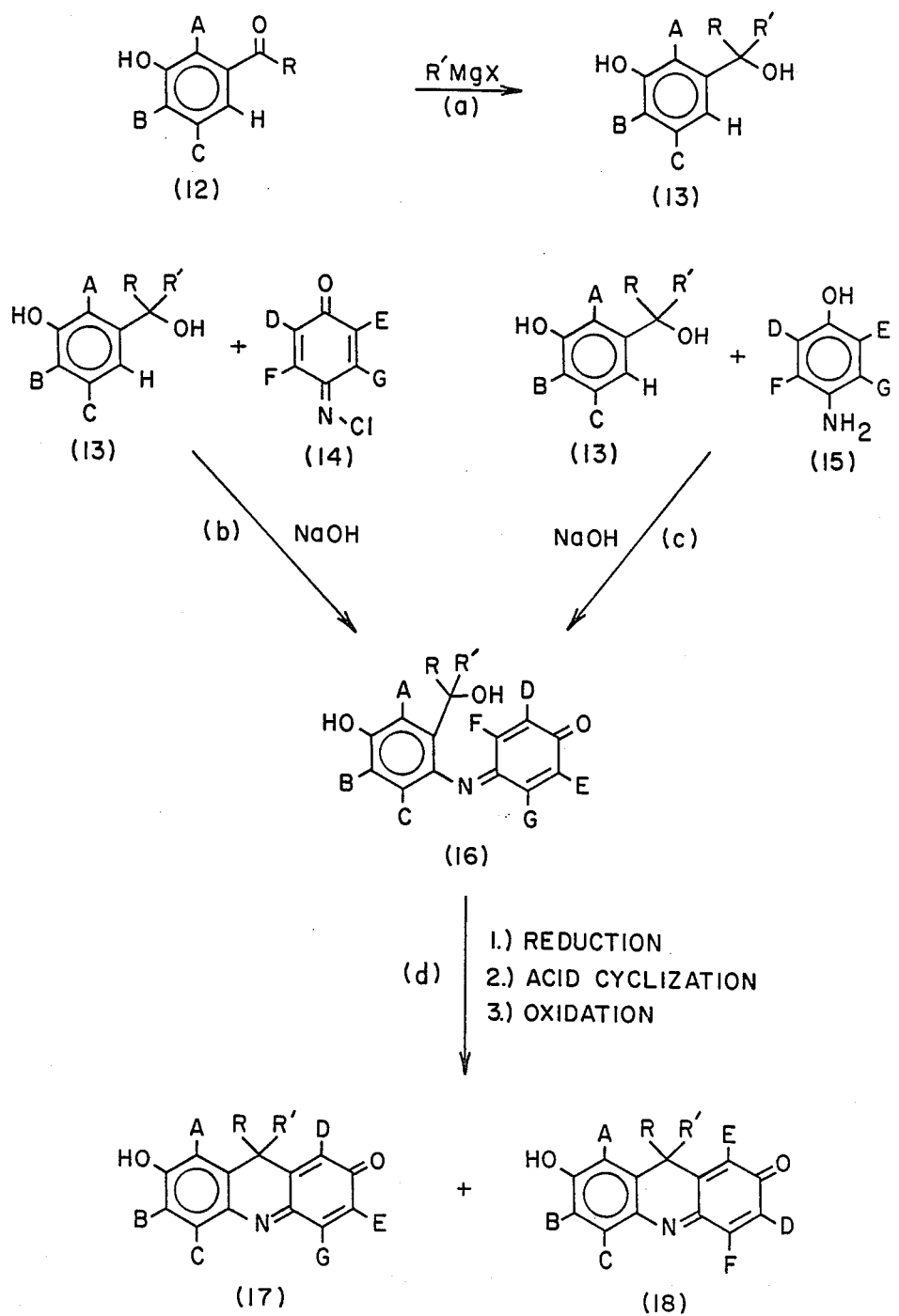
FIG. 1 is a flow diagram of the synthetic pathway for the preparation of the 7-hydroxy-9H-acridin-2-one chromogens.

The chromogenic enzyme substrate compounds of the present invention are derived from 7-hydroxy-9H-acridin-2-one chromogens (hereinafter referred to as acridinones) having the general formula:

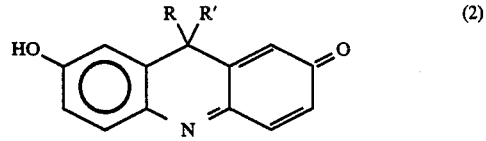

which have been described in the literature where R and R' are phenyl [F. Kehrman and J. Tschui, Helv. Chim. Acta., Vol. 8, p. 23 (1925)] or methyl [H. Goldstein and W. Kopp, Helv. Chim. Acta., Vol. 11, p. 478 (1928)]. The visible absorption spectra of the aforementioned diphenyl and dimethyl chromogens have been described by R. Hill, et al., J. Chem. Soc. (C), 2462 (1970), where a 175 nm shift in absorption ($\lambda_{max}$) between the protonated form and the deprotonated form of such dimethyl and diphenyl chromogens was reported. Such deprotonation occurs in basic solutions, usually from between about pH 7.0 to pH 7.5, at the phenolic hydroxyl group of the chromogen (2) by delocalization of the negative charge of the anion throughout the molecule as follows:

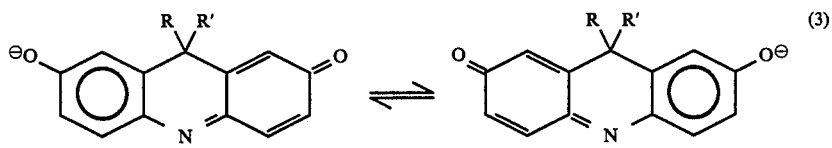

The deprotonated form (3) provides a blue color which is distinct from the yellow color provided by the protonated form (2) thereof.

Similarly, other acridinone analogs have been described by Hill, et al., supra, where, for example, R and R' together form a cyclohexa-2,5-diene-4-one residue [C. Lieberman, Chem. Ber., Vol. 7, p. 1098 (1874), identified as 7-hydroxyspiro[acridine-9,1'-cyclohexa-2',5'-diene]2(9H),4-dione by Hill, et al., supra] to provide chromogens of the formula (4):

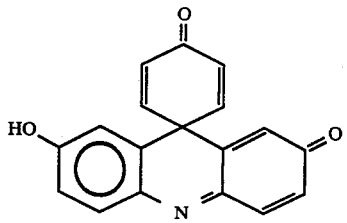

or where R and R' together form a 4-hydroxycyclohexyl residue to provide chromogens of the formula (5):

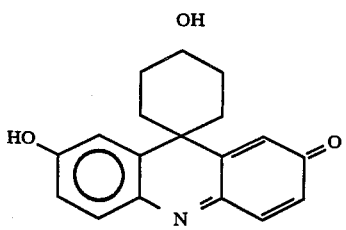

as well as a substituted form of compound (4) to provide chromogen of the formula (6):

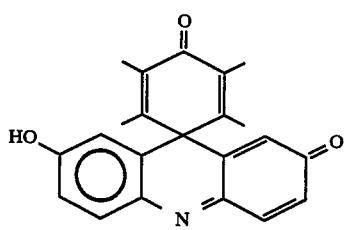

wherein compounds (4), (5) and (6) possess optical properties similar to those exhibited by the acridinone compounds of the general formula (2) and the dimethyl and diphenyl analogs thereof as described above. An acridinone analog (7) of compound (6) has also been described in U.S. Pat. No. 3,781,711 of the formula:

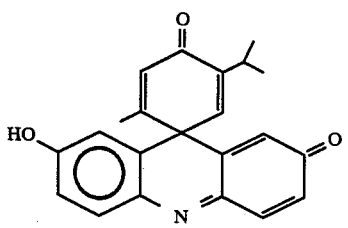

According to the teachings of the present invention, when the phenolic hydroxyl group of the chromogen (2) is derivatized with an enzymatically-cleavable group comprising a radical of a compound Y—OH which is an enzyme-specific moiety, the resulting compounds are novel chromogenic enzyme substrate compounds of the general isomeric formula (8):

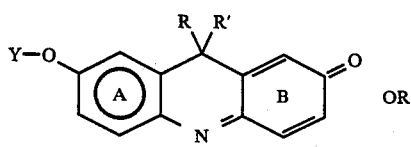

OR

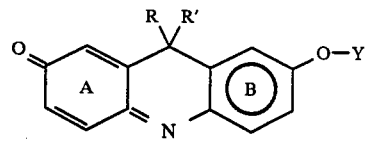

wherein Y represents the enzymatically cleavable group, R and R', which can be the same or different, are alkyl or aryl, or together form a cyclohexadienone residue, preferably a cyclohexa-2,5-diene-4-one residue, or a 4-hydroxycyclohexyl residue. It will be understood that such isomerism of the chromogenic enzyme substrate compound as shown by the structural formula (8) will occur in instances where R and R' are different and/or where either of the aromatic rings A or B is substituted.

It should be undersoood that the present invention describes the first use of the acridinone class of chromogens as indicator groups in chromogenic enzyme substrates and, accordingly, encompass the wide variety of substituted acridinone derivatives. It will be evident that the aromatic rings A and B in the formula (8) can bear a variety of substituent groups without departing from the scope of the present invention. As discussed in greater detail hereinafter, such substituent groups are limited only by the ability of one of ordinary skill in the art to prepare stable compounds which have the chromogenic enzyme substrate properties of the present invention, and include such groups as unsubstituted and substituted alkyl, unsubstituted and substituted aryl, alkoxy, aryloxy, halo (e.g., fluoro, chloro, bromo), nitro and substituted amino uuch as dialkylamino.

In the context of the present invention, "alkyl" is intended to include linear and branched forms of unsubstituted hydrocarbon residues of the general formula—$C_nH_{2n+1}$, preferably of the "lower alkyl" aliphatic type wherein n is 6 or less, uuch as methyl, ethyl, n-propyl, iso-propyl, n-butyl, iso-butyl, tert-butyl, n-hexyl, and the like, as well as substituted forms thereof.

Further in the context of the present invention as used herein, "aryl" is intended to include organic residues derived, from an aromatic hddrocarbon ring or ring system by removal of a hydrogen atom, and include the unsubstituted hydrocarbon ring residues such as phenyl and napthyl, and substituted forms thereof. For purposes of the present invention, aryl residues include those bearing one or more same or different functional groups or substituents which can be selected by one skilled in the art to provide the chromogenic enzyme substrate compounds of the present invention.

More particularly, where "aryl" and "alkyl" are substituted, such substitution is intended to include such groups or substituents when mono- or polysubstituted with functional groups which do not substantially negate the useful features of the present compounds. Such functional groups include chemical groups which may be introduced synthetically and result in the stable and useful chromogenic enzyme substrate indicator compounds of the present invention. Examples of such functional groups include, but are not intended to be limited to, halo (e.g., fluoro, chloro, bromo), substituted amino such as dialkylamino, nitro, alkoxy, aryloxy, alkyl, and aryl.

In particular, where R and/or R' are alkyl, preferably lower alkyl, such alkyl groups include, but are not intended to be limited to, methyl, ethyl, n-propyl, iso-propyl, n-butyl, iso-butyl, tert-butyl, n-hexyl, and substituted forms thereof including, but not necessarily limited to, benzyl, dialkylaminomethyl, more particularly dimethylaminomethyl, or halomethyl, more particularly bromomethyl, and the like. Where R and/or R' are aryl, such aryl groups include, but are not intended to be limited to, napthyl, phenyl, p-chlorophenyl, 2,4-dimethoxyphenyl, and the like.

The chromogenic enzyme substrate compounds (8) possess essentially the same color properties as the protonated form of the chromogen (2), regardless of the pH of the surrounding liquid environment, wherein upon contact of the derivatized chromogenic enzyme substrate compound (8) with an appropriate enzyme in a surrounding environment comprising a basic solution from between about pH 6.5 to pH 10, the enzymatically-cleavable group Y is cleaved by the enzyme to liberate the dissociated or deprotonated form of the chromogen (3) having an absorbance maximum which is substantially greater than the absorbance maximum of the chromogenic enzyme substrate compound (8) to provide a distinct change in the absorbance maximum therebetween. Accordingly, the chromogenic enzyme substrate compound (8) of the present invention is particularly useful in an analytical test system which requires the detection of an enzyme labeled assay reagent employed therein. The distinct and measurable change in the absorbance maximum which is generated between the substrate compound (8) and the deprotonated form of the chromogen (3) can be accurately detected, measured and correlated to the amount of analyte present in a liquid test sample.

Enzymatically-Cleavable Groups

According to the present invention, the enzymatically-cleavable group Y is a radical of a compound Y—OH comprising an enzyme-specific moiety to provide novel chromogenic enzyme substrate compounds which confer specificity to a wide variety of enzymes encountered in clinical chemistry, particularly hydrolases. The compound Y—OH is intended to include, but is not necessarily limited to, sugars and derivatives thereof, acyl groups including aliphatic and aromatic carboxylic acids, amino acids and peptides, and inorganic acids such as phosphoric and sulfuric acid groups.

It is to be understood that it will be evident to one skilled in the art that the selection of the enzymatically-cleavable group Y will depend, of course, upon the particular enzyme of interest. For example, where the enzyme of interest is a glycosidase, a glycoside can be prepared in which the enzymatically-cleavable group Y is the glycosidic radical corresponding to the natural substrate for the particular glycosidase. Suitable glycosidic radicals include, but are not intended to be limited to, mono- and oligosaccharide radicals, which are capable of being incorporated into a glycoside substrate specific for a particular glycosidase enzyme and cleaved by said enzyme, such as radicals of β-D-galactopyranose, α-D-galactopyranose, β-D-glucopyranose, α-D-glucopyranose and α-D-mannopyranose, as well as amino sugars such as N-acetylglucosamine and N-acetylneuraminic acid, and the like radicals. Other suitable glycosidic radicals include oligosaccharide chains from between about 2 to 20, preferably 2 to 7, monosaccharide units attached by α-1-4 glucosidic linkages, which can be broken down by saccharide-chain splitting enzymes to a mono- or oligosaccharide which, in turn, can be cleaved by a corresponding glycosidase, such as, for example, radicals of maltopentose, maltohexose and maltoheptose.

It is to be understood that in some instances where the glycosidic radical is an oligosaccharide chain as heretofore described, such chain is first modified or broken down to a shorter oligosaccharide or monosaccharide by the enzyme under determination to produce a secondary substrate compound in which the enzymatically-cleavable group is cleaved from the acridinone indicator group by a secondary enzyme, in which case the secondary substrate compound is then contacted with the secondary enzyme to generate a measurable change in absorbance as heretofore described. For example, where the enzyme under determination is α-amylase, the oligosaccharide chain is cleaved to produce a secondary glycoside substrate compound, e.g., an α-glucoside or β-glucoside, in which the resulting glycoside group thereof is cleavable from the acridinone indicator group by a secondary glycosidase enzyme, e.g., α-glucosidase or β-glucosidase, respectively.

In the case of nonspecific esterase enzymes, the enzymatically-cleavable group Y is an acyl radical group to provide a chromogenic ester of the formula (9):

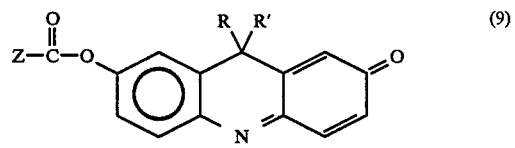

Where Z is lower alkyl or aryl, such compounds can be employed for the detection of nonspecific esterase enzymes such as cholinesterase, acylase, lipase, and the like.

The chromogenic enzyme substrate compounds of the present invention can also be utilized for the detection of proteolytic enzymes commonly found in leukocytes. Such compounds are esters of the general formula (8) where Y is a radical of the compound Y—OH and where Y—OH is an N-protected amino acid or short peptide, e.g., consisting of between about 2 to 5 amino acid units. For example, where Y is the radical of the N-protected amino acid N-tosyl-L-alanine and R and R' are defined as above, the ester is represented by the formula (10):

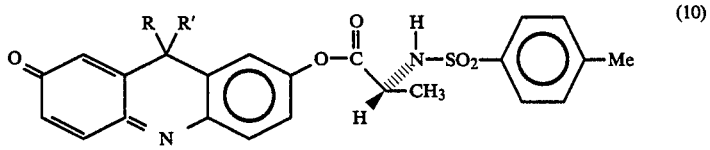

It will be appreciated that the present invention contemplates other carboxylic acid residues, amino acid residues and N-protecting groups as equivalents, as will be described in greater detail hereafter.

Similarly, for the detection of alkaline phosphatase from a liquid test sample, the enzymatically-cleavable group Y is a radical of the compound Y—OH wherein Y—OH is a phosphoric acid group to provide a chromogenic phosphate ester of the formula (11:

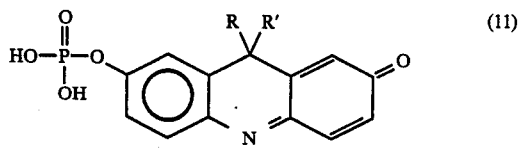

(11)

Preparation of Chromogenic Acridinone Enzyme Substrate Compounds

The chromogenic acridinone enzyme substrate compounds (8) of the present invention can be prepared by reacting the compound Y—OH, where Y is a selected enzymatically cleavable group, with an appropriately derivatized 7-hydroxy-9H-acridin-2-one chromogen, as will be described in greater detail hereinafter, under condensation reaction conditions known in the art. Generally, the appropriate acridinone chromogen is coupled under appropriate conditions with a reactive derivative of the compound Y—OH, preferably a carbohydrate (sugar) or carbohydrate-derivative or an acid as heretofore described, to provide a chromogenic acridinone enzyme substrate having the desired stereoisomerism.

As stated above, the present invention contemplates various substituents which can be substituted at the aromatic rings A and B of the acridinone nucleus in the formula (8) as equivalents to the substrate compounds of the formula (8). Substituted equivalents are prepared through the use of appropriately derivatized 7-hydroxy-9H-acridin-2-ones which can be prepared (FIG. 1) according to methods known in the art employing, as starting materials, a 3-hydroxyacetophenone or a 3-hydroxybenzophenone (12) and an appropriate Grignard reagent which are reacted [reaction (a)] to result in a substituted phenol (13) which, in turn, is reacted [reaction (b)] with a substituted benzoquinone-N-chloroimine (14) to result in a functionalized indophenol (16). The indophenol (16) is then reduced to its leuko form, acid cyclized, and then oxidized [reaction (d)] to result in the desired 7-hydroxy-9H-acridin-2-one (17 and 18). It is to be appreciated that selection of appropriately derivatized starting materials and an appropriate Grignard reagent results in a variety of substituted phenols and, accordingly, one skilled in the art of organic chemical synthesis can prepare specific indophenols having a variety of substituents which can be converted to a desired appropriately derivatized 7-hydroxy-9H-acridin-2-one for use as the chromogen of the chromogenic acridinone enzyme substrate compounds of the present invention.

In particular, the phenols (13) are prepared according to the method described by Hill, et al., supra, where R and R' can both be methyl or phenyl and A, B and C are hydrogen, from the corresponding 3-hydroxyacetophenone or 3-hydroxy-benzophenone (12) which are reacted with [reaction (a)] a methylmagnesium bromide Grignard reagent or phenylmagnesium iodide Grignard reagent respectively. It is to be appreciated that the Grignard reagent can be selected from a wide variety of such reagents which have been described in the art and include, but are not necessarily limited to alkyl and aryl Grignard reagents, such as where X represents bromine or iodine, as well as those bearing functional group substituents such as —O—alkyl (alkoxy), —O—aryl (aryloxy), -alkyl and -aryl. Similarly, the synthesis of a variety of substituted 3-hydroxyacetophenones (12) where R can be alkyl or substituted alkyl, and 3-hydroxybenzophenones (12) where R can be aryl or substituted aryl, have been described and include compounds of the general formula (12) where R, A, B and C can be selected from a wide variety of susstituents known in the art. For example, R can be methyl, A and C can be hydrogen, and B can be bromo, chloro, iodo, methyl or cyclohexyl [*J. Med. Chem.*, Vol. 23, p. 738(1980)]; or R and C can be methyl, A and B can be nitro and hydrogen or hydrogen and nitro, respectively, or A and B can be hydrogen [*Chem. Ber.*, Vol. 92, p. 2172(1959)]; or R can be methyl, A and C can be hydrogen, and B can be methoxy [*Chem. Ber.*, Vol. 55B, p. 1892(1922)] or cyclohexylether [*J. Chem. Soc.*, p. 3430(1951)]; or R and A can be methyl, B can be hydrogen, and C can be nitro [*J. Org. Chem.*, Vol. 14, p. 397(1949)]; or R can be methyl, A and B can be methoxy, and C can be hydrogen [*J. Prakt. Chem.*, Vol. 103, p. 329(1922)]; or R can be methyl, A and C can be hydrogen, and B can be p-hydroxyphenol [*Hoppe-Seyler's Z. Physiol. Chem.*, Vol. 292, p. 58(1953)]; or A, B and C can be hydrogen, and R can be dimethylaminomethyl [*Monatsh.*, Vol. 80, p. 517(1949)] or benzyl or phenylethyl [*Medd. Norsk. Farm. Selskap.*, Vol. 24, p. 45(1962)] or p-chlorophenyl [*J. Chem. Soc.*, p.5(1946)] or 2,4-dimethoxyphenyl [*Bull. Soc. Chim. France*, p. 1682(1959)]; or R can be bromomethyl and where A, B or C is nitro, then B and C, A and C or A and B can be hydrogen, respectively [*Acta Univ. Szeged., Acta Phys. Chem.*, Vol. 9, p. 48(1963)]; or R can be phenyl and A and C can be hydrogen and B can be methyl [*Helv. Chim. Acta.*, Vol. 29, p. 1413(1946)] or A and B can be methoxy and C can be hydrogen [*J. Org. Chem.*, Vol. 24, p. 952(1959)]; and the like.

The desired indophenol (16) is prepared by reacting the appropriately substituted phenol (13) resulting from reaction (a) with an appropriately substituted benzoquinone-N-chloroimine (14) in aqueous alkali [reaction (b)] as described by Hill, et al, supra, where R and R' can both be methyl or phenyl and all of A-G can be hydrogen, and as described more generally by Gibbs, et al., Supplement No. 69 to the *Public Health Reports*, Washington, D.C. (1928), where all of substituents D, E, F and G in the general structure (14) can all be hydrogen, or D can be methyl and E, F and G can be hydrogen, or D, E and G can be hydrogen and F can be methyl, or D and E can be chlorine or bromine and F and G can be hydrogen, respectively. An alternate synthetic pathway for the preparation of the indophenol (16) is also described by Corbett, *J. Chem. Soc.* (B), p. 1502 (1970) where an appropriately substituted phenol (13) is reacted with an appropriately substituted p-aminophenol (15) and oxygen in the presence of aqueous alkali [reaction (b)]. The substituents D, E, F and G of the p-aminophenol (15) are described where D, E and G can be hydrogen and F can be methyl or chlorine, or D, F and G can be hydrogen and E can be methyl, or D and G can be methyl and E and F can be hydrogen, or D and E can be methyl or chlorine and F and G can be hydrogen, or D can be chlorine and E, F and G can be hydrogen, respectively.

The indophenol (16) resulting from either reaction (b) or (c) is then employed to prepare the 7-hydroxy-9H- acridin-2-ones (17) and (18) according to the method described by Hill, et al., supra, [reaction (d)] where the indophenol (16) is reduced (step 1) to its leuko form with, for example, tin (II) chloride in aqueous acid or other mild reducing agents known in the art such as sodium hydrosulfite, sodium borohydride and the like. The resulting leuko intermediate is cyclized (step 2) by heating the intermediate in aqueous mineral acid, preferably 2N HCl, for approximately 1 hour at 90°–100° C., and then oxidized (step 3) with, for example, air ($O_2$) in aqueous alkali or a variety of other chemical oxidants such as potassium ferricyanide or alkali metal periodates, preferably sodium periodate, and the like. It is to be appreciated that it is not necessary to isolate the various intermediates resulting from steps 1–3 of reaction (d) to obtain satisfactory yields of the acridinones (17) and (18).

According to a preferred embodiment of the present invention, novel 7-hydroxy-1,3-dihalo-9H-acridin-2-one derivatives of the tautomeric formula (19):

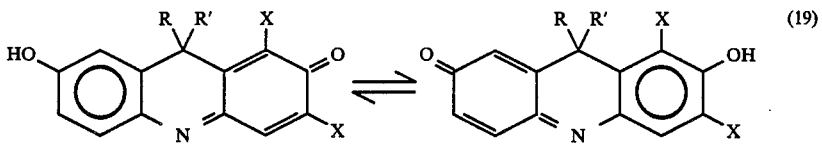

are also provided where R and R', which can be the same or different, are alkyl or aryl as heretofore described, preferably lower alkyl or phenyl, and X is a halo radical, preferably bromo or chloro. Such intermediates are particularly useful for the preparation of a dimethyl acridinone chromogen (20) (FIG. 2) which can then be reacted with a radical Y of the Y—OH compound to provide the chromogenic enzyme substrate compounds of the present invention.

Figure 2:
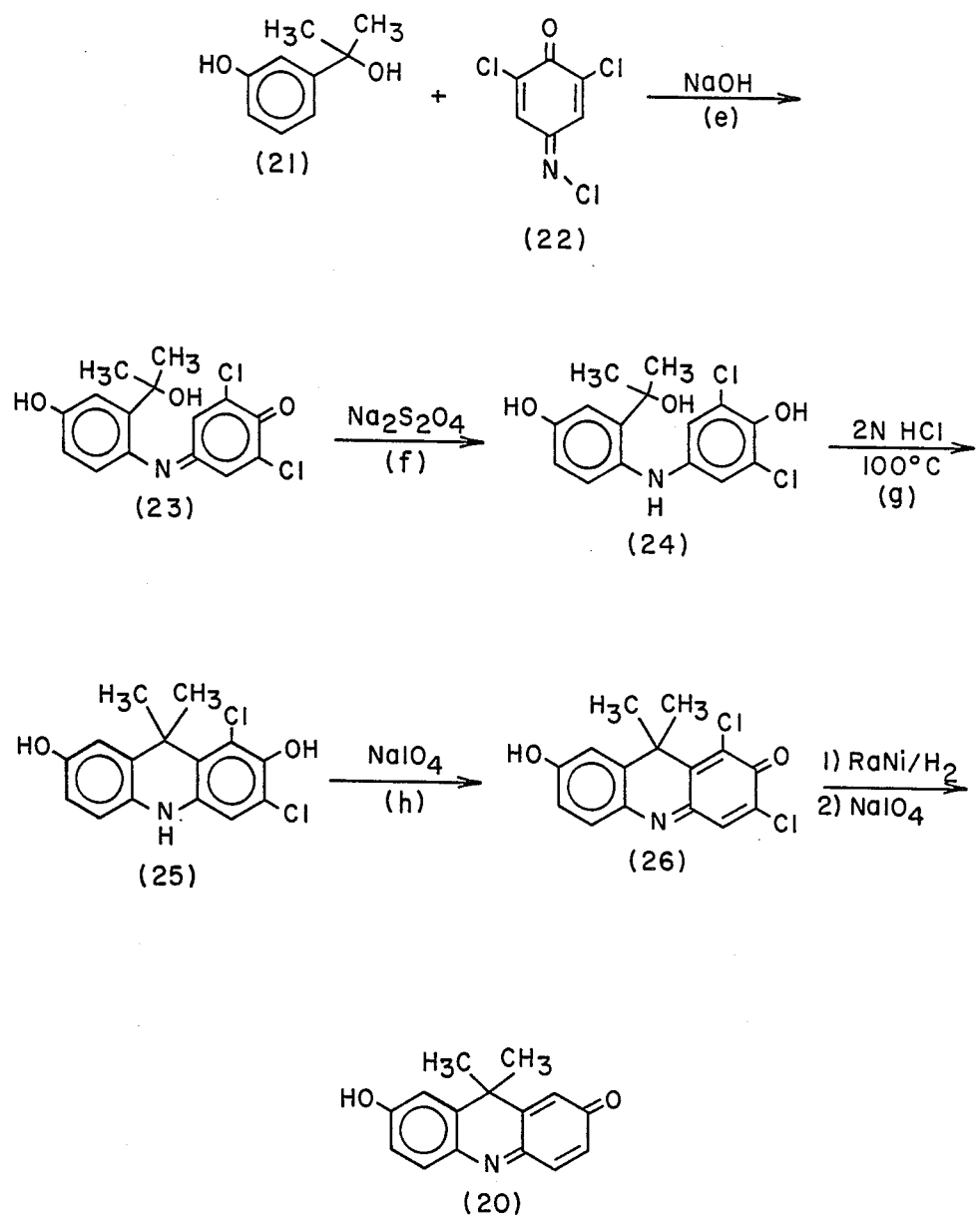
FIG. 2 is a flow diagram of the synthetic pathway for the preparation of the 7-hydroxy-9,9-dimethyl-9H-acridin-2-one chromogens employing the 7-hydroxy-1,3-dichloro-9,9-dimethyl-9H-acridin-2-one intermediate.

In particular, as illustrated in FIG. 2, the dimethyl acridinone chromogen (20) can be prepared by first reacting 3-(1-hydroxy-1-methylethyl)phenol (21) [Bruce, et al., *J. Chem. Soc.* (C), 1627(1966)] and 2,6-dichloroquinone-4-chloroimide (22) [Gibbs, et al., *U.S. Public Health Reports,* Supp. 69 and *Chem. Abs.*, Vol. 23, 3450(1929)] with sodium hydroxide in aqueous tetrahydrofuran [reaction (e)] under appropriate conditions to result in the dichloro-substituted indophenol (23), which is then reduced [reaction (f)] to result in compound (24), acid cyclized [reaction (g)] to result in compound (25), and then oxidized [reaction (h)] to result in the novel 7-hydroxy-1,3-dichloro-9,9-dimethyl-9H-acridin-2-one (26) of the present invention. The dichloro-derivative (26) is first treated with (1) Raney Nickel and hydrogenated, and then treated with (2) sodium periodate to result in the dimethyl acridinone chromogen (20).

Figure 3:
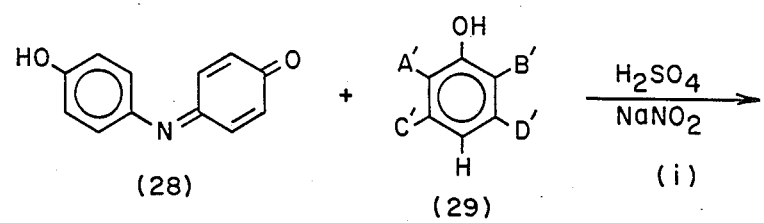
FIG. 3 is a flow diagram of the synthetic pathway for the preparation of the 7-hydroxyspiro [acridin-9,1'-cyclohexa-2',5'-diene]-2(9H)4-dione chromogens and analogs thereof.
Figure 3:
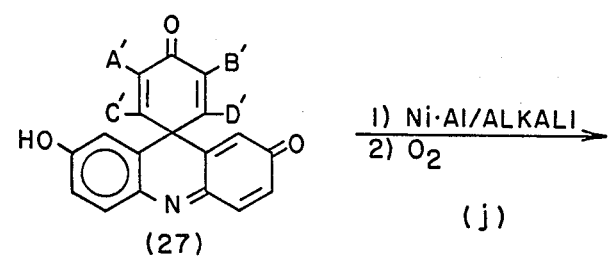
Figure 3:
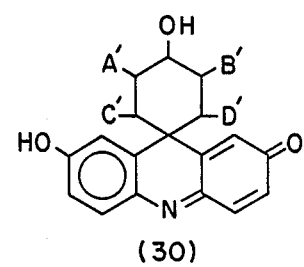

Although R and R' in the acridinones (17) and (18) can be selected from a variety of substituents as heretofore described, R and R' can also together form a cyclic moiety and are prepared according to the method described by Hill, et al., supra, (FIG. 3) having the general structure (27) (7-hydroxyspiro[acridin-9,1'-cyclohexa-2',5'-diene]-2(9H),4'-dione). Such compounds (27) are prepared by reacting indophenol (28) with an appropriately substituted phenol (29) in sulfuric acid with sodium nitrite [reaction (i)] where A', B', C' and D' can all be hydrogen or methyl, or A' and B' can be hydrogen or methyl and C' and D' can be methyl or hydrogen, respectively, or A' can be methyl and B', C' and D' can be hydrogen, or A', B' and D' can be hydrogen and C' can be methyl. Where A', B', C' and D' are all hydrogen, compound (27) can be reduced with nickel-aluminum alloy in aqueous sodium hydroxide [reaction (j)] to result in the saturated analog thereof (30). Similarly, acridinones of the formula (27) have been described where A' can be isopropyl, D' can be methyl, and B' and C' can be hydrogen (U.S. Pat. No. 3,781,711).

The glycosides of the acridinone derivatives of the general formula (8) can be prepared according to methods known in the art of carbohydrate chemistry employing known derivatives of carbohydrates of the formula Y—OH which are reacted with an appropriate chromogen (2). Such carbohydrate derivatives, which in some instances carry protecting groups, are commercially available (Aldrich Chemical Co., Milwaukee, Wis., U.S.A.; Sigma Chemical Co., St. Louis, Mo., U.S.A.), or can be prepared according to methods known in the art [*Methods in Carbohydrate Chemistry* (Academic Press, 1963), Vol. 2]. Glycosidic radicals which are suitable for coupling to the acridinone derivatives of the general formula (2) to provide glycosides of the general formula (8), include, but are not intended to be limited to, radicals of sugars such as β-D-galactopyranose, α-D-galactopyranose, β-D-glucopyranose, α-D-glucopyranose, α-D-mannopyranose, N-acetylglucosamine, β-glucuronic acid and neuraminic acid. Other suitable glycosidic radicals include radicals of oligosaccharide chains which by saccharide-chain splitting enzymes can be broken down to the level of a mono- or oligosaccharide, which in its turn can be directly split off from the acridinone skeleton with the corresponding glycosidase. It is to be understood that such oligosaccharide chains are chains consisting of 2 to 20, preferably 2 to 7 monosaccharide units, such as maltopentose, maltohexose or maltoheptose. The acridinone derivatives of the general formula (2) are reacted with a mono- or oligosaccharide or a 1-halogeno-derivative thereof, where all hydroxyl groups are substituted with a protecting group according to methods known in the art of carbohydrate chemistry, to give per-O-substituted glycosides, from which the glycosides of the acridinone-derivatives of general formula (8) are obtained by splitting off the protective groups according to methods known in the art.

The compounds of the general formula (2) are reacted with the per-O-substituted 1-halogenosaccharides, preferably in the presence of proton acceptors such as alkali hydroxides or alkali carbonates, in aqueous acetone or (under phase transfer conditions) in a water/chloroform or water/benzene mixture. This procedure can furthermore be carried out by first converting the acridinone-derivative of general formula (2) with alkali hydroxide or alcoholate into alkali salts or, using possibly substituted amines, into ammonium salts, and then reacting these with the per-O-substituted 1-halogeno saccharides in dipolar aprotic solvents such as acetone, dimethylsulfoxide, dichloromethane, tetrahydrofuran or dimethylformamide. Furthermore in the synthesis of per-O-substituted glycosides from acridinone-derivatives of the general formula (2) and per-O-substituted 1-halogenosaccharides, additives in the form of single silver salts or mixtures of silver salts, such as silver oxide, silver carbonate, silver carbonate on Celite® (Johns-Manville Corp., Denver, Co., U.S.A.), silver triflate or silver salicylate, and/or of single mercury salts or mixtures of mercury salts, such as mercury bromide, mercury cyanide, mercury acetate or mercury oxide, and/or of single cadmium salts or mixtures of cadmium salts such as cadmium carbonate or cadmium oxide, possibly with the use of drying agents such as calcium chloride, a molecular seive or Drierite® (W. A. Hammond Drierite Co., Xenia, Ohio, U.S.A.), in solvents such as methylene chloride, chloroform, benzene, toluene, ethyl acetate, quinoline, tetrahydrofuran or dioxane have proven effective. In the synthesis of α-linked glycosides, a compound of the general formula (2) is melted with a saccharide whose hydroxy groups are substituted with a protective group, preferably an acetyl-group, in the presence of a Lewis acid, such as zinc chloride [see *Chem. Ber.* 66, 378-383 (1933) and *Methods in Carbohydrate Chemistry* (Academic Press, 1967) Vol. 2, pp. 345-347]. The temperature of the reaction is preferably between 80° and 130° C., more preferably between 110° and 130° C. The resulting per-O-substituted glycosides of acridinone-derivatives of general formula (2) likewise are new compounds. Removing the protecting groups from the per-O-substituted glycosides to form glycosides of general formula (8) is performed according to methods known in the art of carbohydrate chemistry [see *Advances in Carbohydrate Chem.* 12, 157 (1976)], such as with the protective acyl-groups with sodium methylate, barium methylate or ammonia in methanol. Suitable as a "protecting group" commonly used in carbohydrate chemistry is especially an acetyl, benzoyl, benzyl or trimethylsilyl-radical.

Acridinone derivatives of the general formula (8) where Y is the radical of an oligosaccharide chain of from about 2 to 20 monosaccharide units attached via α-1-4 glucosidic linkages can additionally be prepared from α- and β-acridinone glucosides by an enzymatic process first described by French, et al., *J. Am. Chem. Soc.* 76, 2387 (1954), and later by Wallenfels, et al., *Carbohydrate Research* 61, 359 (1978), involving the transfer of the glucoside to a pre-formed polysaccharide chain by the enzyme (1–4)-α-glucan-4-glucosyltransferase (also known as cyclomaltodextrin glucanotransferase; EC 2.4.1.19).

According to a preferred embodiment of the present invention, chromogenic enzyme substrate compounds of the general formula (8), where Y is a radical of an enzyme-specific sugar moiety Y—OH, preferably β-D-galactose or β-D-glucose, and R and R' are methyl, can be prepared by reacting the dimethyl chromogen (20) with a 1-halogeno-derivative of the enzyme-specific moiety, preferably a 1-bromo-derivative thereof, substituted at the hydroxy-positions thereof with protecting groups, preferably acetate protecting groups, to result in per-O-substituted derivatives which can be hydrolyzed to remove such protecting groups to obtain the desired chromogenic enzyme substrate compound. For example, the β-D-galactoside of (20), the chromogenic enzyme substrate (8) where Y is the radical of β-D-galactose and R and R' are methyl, can be prepared for use in the determination of β-D-galactosidase. In particular, the dimethyl acridinone chromogen (20), where R and R' are methyl in the general formula (2), is reacted with acetobromogalactose and silver oxide in ethyl acetate/quinoline to prepare the 7-(tetra-O-acetyl-β-D-galactopyranosyloxy)-9,9-dimethyl-9H-acridin-2-one (31) of the formula:

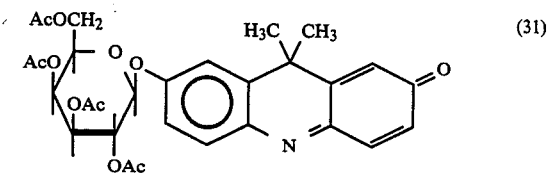

The acetate protecting groups of (31) are then hydrolyzed with sodium methoxide in methanol to result in the desired 7-β-D-galactopyranosyloxy-9,9-dimethyl-9H-acridin-2-one (32) of the present invention of the formula:

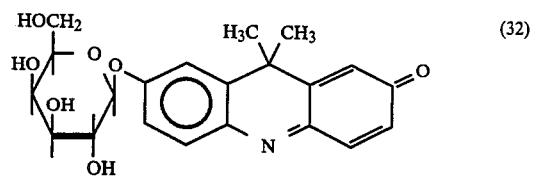

The resulting galactoside (32) has an absorbance ($\lambda_{max}$) of 438 nm (yellow), an extinction coefficient of 27,400, and is soluble in a phosphate buffered solution (pH 7.4). Upon the hydrolysis of the galactoside by β-D-galactosidase from a liquid test sample, the liberated chromogen anion is soluble in the phosphate buffered solution and exhibits an absorbance of 634 nm (blue) to provide a 196 nm change in absorbance. Further, the enzyme cleaves the substrate ($K_{cat}$) at the rate of $1.32 \times 10^4$ mol. min.$^{-1}$/mol. active site in a 50 mM phosphate buffered solution (pH 7.4) containing 5 mM $MgCl_2$, and exhibits a binding constant ($K_m$) of 0.17 mM, and, accordingly, provides a very advantageous substrate for β-D-galactosidase.

The β-D-glucoside of (20), the chromogenic enzyme substrate (8) where Y is the radical of β-D-glucose and R and R' are methyl, can be similarly prepared by reacting the dimethyl acridinone chromogen (20) with acetobromoglucose and silver oxide in quinoline to prepare the 7-(tetra-O-acetyl-β-D-glucopyranosyloxy)-9,9-dimethyl-9H-acridin-2-one (33) of the formula:

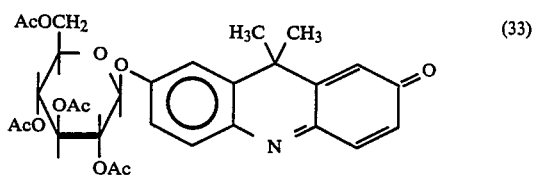

The acetate protecting groups of (33) are then hydrolyzed with sodium methoxide in methanol to result in the desired 7-β-D-glucopyranosyloxy-9,9-dimethyl-9H-acridin-2-one (34) of the present invention of the formula:

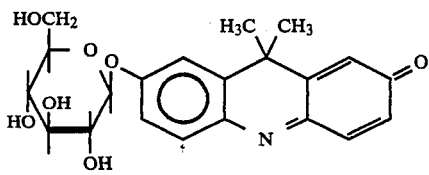

(34)

The esters of acridinone-derivatives of the general formula (9) can be prepared by methods known in the art of organic chemistry by reacting known derivatives of carboxylic acids of the formula Y—OH, where Y=-Z—C— and where Z is defined the same as R and R' above, with the acridinone derivative of the general formula (2). Such known derivatives of carboxylic acids of the formula Y—OH include, but are not intended to be limited to, amino acid residues, preferably residues of naturally-occurring α-amino acids in their L- or D-form or also in their racemic form, the residues of glycine, alanine, valine, leucine, isoleucine, phenylalanine and tyrosine being preferred, the L- forms thereof being more preferred. Any free hydroxyl groups possibly present may be acylated and preferably acetylated. The peptide residues in this definition of Y—OH are to be understood to be, for example, amino acids or peptides from between about 2 to 5 amino acid units such as di-, tri-, tetra-, and pentapeptides, di- and tripeptides being preferred, the amino acid components thereof being the above-mentioned amino acids. It is also to be understood that the amino groups of such amino acids or peptides may be protected with nitrogen protecting groups known in the art of peptide chemistry [see T. W. Green, *Protective Groups in Organic Synthesis* (J. Wiley and Sons, New York, N.Y., 1981), pp. 218–287] including, for example, acyl, oxycarbonyl, thiocarbonyl, sulphonyl, especially p-toluenesulphonyl (Tosyl, Ts), sulphenyl, vinyl, cyclohexenyl, and carbamoyl, especially t-butyl-(BOC) and benzyl-(CBz) carbamoyl radicals. According to a preferred embodiment of the present invention, an especially preferred N-protected amino acid radical is N-tosyl-L-alanine which can be prepared according to the method described by Beecham, *J. Am. Chem. Soc.*, Vol. 79, p. 3257(1957) and then reacted with thionyl chloride to provide the N-tosyl-L-alaninyl chloride intermediate (35) of the formula:

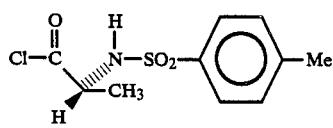

(35)

which can then be reacted with the dimethyl acridinone chromogen (20) in tetrahydrofuran and pyridine to provide the 7-(N-tosyl-L-alaninyloxy)-9,9'-dimethyl-9H-acridin-2-one (36) of the formula:

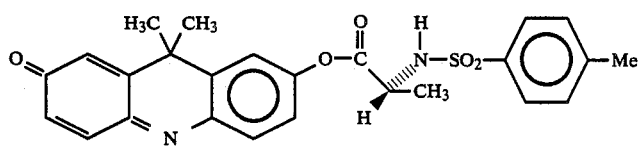

(36)

Such esters may also be similarly prepared by reacting a compound of the general formula (2) with a carboxylic acid, amino acid or peptide, Y—OH as defined above, or with an appropriate reactive derivative thereof, employing metoods known in the art of organic chemistry [see J. March, *Advanced Organic Chemistry: Reactions, Mechanism and Structure* (McGraw-Hill Book Co., New York, N.Y., 1968) pp. 319–323]. The reactive derivatives used can be, for example, acid chlorides or bromides, or mixed anhydrides conventionally used in peptide synthesis, such as those with ethyl chloroformate, or active esters such as those of N-hydroxysuccinimide.

Similarly, inorganic esters of the acridinone-derivatives of the general formula (8) can be prepared according to methods known in the art of organic synthesis. The known derivatives of inorganic acids Y—OH, such as phosphoric acid, e.g., compound (11) where

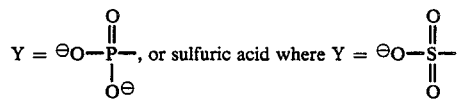

are reacted with a compound of the general formula (2) employing methods known in the art of organic chemistry, such as shown in Koller and Wolfbeis, *Monatsh.* 116, 65 (1985) for inorganic esters of certain coumarins.

According to a preferred embodiment of the present invention, the dimethyl chromogen compound (20) in pyridine can be reacted first with phosphorous oxychloride (POCl$_3$) and then aqueous sodium hydroxide to result in disodium-9,9-dimethyl-9H-acridin-2-one-7-phosphate (37) of the formula:

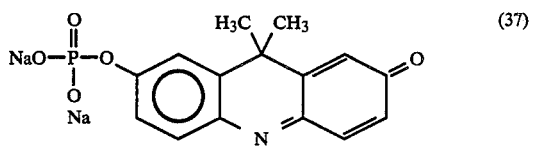

(37)

which is hydrolysed by alkaline phosphatase in 1.0M diethanolamine buffer (pH=9.8) containing 5.0 mM MgCl$_2$ and exhibits a K$_M$=0.48 mM and a K$_{cat}$=1.94×10$^5$ mol/min/mol of enzyme. A reference compound, p-nitrophenylphosphate, under the same conditions has K$_M$=0.97 mM and K$_{cat}$=4.16×10$^{55}$ mol/min/mol of enzyme.

Analytical Test Systems

The chromogenic enzyme substrate compounds of the present invention are useful in analytical test systems which require the measurement of the amount of enzyme present therein, particularly those analytical test systems employing enzyme-labeled assay reagents. Such analytical test systems include, but are not intended to be limited to, enzyme immunoassays known in the art as competitive, sandwich and immunometric techniques where the amount of enzyme label in a particular fraction thereof can be measured and correlated to the amount of analyte under detrmination obtained from a liquid test sample.

The use of specific binding substances, such as antigens, haptens, antibodies, lectins, receptors, avidin, and other binding proteins, and polynucleotides, labeled with an enzyme have been recently developed and applied to the measurement of substances in biological fluids (see, for example, *Clin. Chem.,* Vol. 22, p. 1232 (1976); U.S. Pat. No. Re. 31,006; and U.K. Pat. No. 2,019,308). Generally, such measurement depends upon the ability of a binding substance, e.g., an antibody or an antigen, to bind to a specific analyte wherein a labeled reagent comprising such binding substance labeled with an enzyme is employed to determine the extent of such binding. Typically, the extent of binding is determined by measuring the amount of enzyme label present in the labeled reagent which either has or has not participated in a binding reaction with the analyte, wherein the amount of enzyme detected and measured can be correlated to the amount of analyte present in a liquid test sample.

The chromogenic enzyme substrate compounds of the present invention are particularly useful in analytical test systems as heretofore described where an analytical test device comprising a carrier matrix incorporated with the chromogenic enzyme substrate compound of the present invention is employed, the nature of the enzyme-specific moiety thereof depending, of course, upon the particular enzyme being detected.

The nature of the material of such carrier matrix can be of any substance capable of being incorporated with the chromogenic enzyme substrate compound of the present invention, such as those utilized for reagent strips for solution analysis. For example, U.S. Pat. No. 3,846,247 describes the use of felt, porous ceramic strips, and woven or matted glass fibers. As substitutes for paper, U.S. Pat. No. 3,552,928 describes the use of wood sticks, cloth, sponge material, and argilaceous substances. The use of synthetic resin fleeces and glass fiber felts in place of paper is suggested in British Pat. No. 1,369,139, and British Pat. No. 1,349,623 teaches the use of a light-permeable meshwork of thin filaments as a cover for an underlying paper matrix. This reference also teaches impregnating the paper with part of a reagent system and impregnating the meshwork with other potentially incompatible reagents. French Pat. No. 2,170,397 describes the use of carrier matrices having greater than 50% polyamide fibers therein. Another approach to carrier matrices is described in U.S. Pat. No. 4,046,513 wherein the concept of printing reagents onto a suitable carrier matrix is employed. U.S. Pat. No. 4,046,514 describes the interweaving or knitting of filaments bearing reagents in a reactant system. All such carrier matrix concepts can be employed in the present invention, as can others. Preferably, the carrier matrix comprises a bibulous material, such as filter paper, whereby a solution of the chromogenic enzyme substrate compound of the present invention is employed to impregnate the matrix. It can also comprise a system which physically entraps the assay reagents, such as polymeric microcapsules, which then rupture upon contact with the test sample. It can comprise a system wherein the assay reagents are homogeneously combined with the carrier matrix in a fluid or semi-fluid state, which later hardens or sets, thereby entrapping the assay reagents.

In a preferred embodiment, the carrier matrix is a bibulous material in the form of a zone or layer incorporated with the chromogenic enzyme substrate compound of the present invention which is employed where a particular assay is performed in a liquid environment employing an insoluble assay reagent known in the art to physically separate the free species of the labeled reagent from the bound species of the labeled reagent. According to such assay system, an aliquot of liquid containing the free species is removed and applied to the carrier matrix wherein the chromogenic enzyme substrate compound incorporated therein interacts with the enzyme label of the labeled reagent of the free species from the liquid test sample to provide a detectable signal which can be visibly observed and/or measured with an appropriate instrument, such as a spectrophotometer.

Similarly, a test device comprising two or more carrier matrices in the form of, for example, an uppermost layer or zone and a lowermost layer or zone can be employed. The lowermost layer of such test device can be incorporated with the chromogenic enzyme substrate compound of the present invention wherein a liquid test sample containing analyte under determination is applied to the uppermost layer of the device. The analyte which diffuses therein participates in the necessary binding reactions to generate a free and bound (i.e., immobilized) species of the enzyme labeled reagent therein as heretoforedescribed. Accordingly, the free species of the labeled reagent so generated is free to migrate into the lowermost layer where the enzyme label of the free species cleaves the enzymatically-cleavable group of the chromogenic enzyme substrate compound of the present invention incorporated therein to provide a measurable, detectable signal as heretofore described.

The present invention will now be illustrated, but is not intended to be limited, by the following examples. Italicised numbers in parenthesis refer to the structural formulae as used in the figures and/or the specification.

EXAMPLE 1 Synthesis and Analysis of 7-Hydroxy-9,9-dimethyl-9H-acridin-2-one (20).

In order to demonstrate the suitability of the chromogen (2) for use as an indicator in the chromogenic enzyme substrate compounds of the present invention, the 7-hydroxy-9,9-dimethyl-9H-acridin-2-one chromogen (20) of the formula:

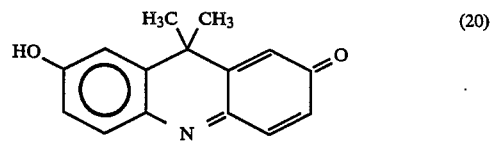

was prepared according to the method of Hill, et al., *J. Chem. Soc.* (C), 2462 (1970), where R and R' in the general formula (2) are methyl. Upon analysis of the dimethyl chromogen (20), such chromogen was determined to have a phenolic $pK_a$ of 7.1, an absorbance ($\lambda_{max}$) of 459 nm, and to be soluble and stable in aqueous, basic solutions. When the dimethyl chromogen (20) was deprotonated, the anion thereof exhibited an absorbance of 635 nm and an extinction coefficient of 53,100 at pH=10 to provide a 176 nm shift in the absorbance maximum and high extinction coefficient necessary for the chromogenic enzyme substrate compounds of the present invention.

EXAMPLE 2

Synthesis of 7-Hydroxy-9,9-dimethyl-9H-acridin-2-one (20) From 7-Hydroxy-1,3-dichloro-9,9-dimethyl-9H-acridin-2-one Intermediate (26) (FIG. 2).

(a) Synthesis of 7-Hydroxy-1,3-dichloro-9,9-dimethyl-9H-acridin-2-one (26)

A mixture of 2-(3'-hydroxyphenyl)-2-propanol (21) (1.52 g; 10.0 mmol) prepared as described by Bruce, et al., *J. Chem. Soc.* (C), 1627 (1966) and 2,6-dichloroquinone-4-chloroimide (22) (Aldrich Chemical Co., Milwaukee, Wis., U.S.A.) (2.10 g; 10.0 mmol) in tetrahydrofuran (5 mL) was diluted with $H_2O$ (5 mL), chilled in an ice bath and dropwise treated, over 10 min, with aqueous 2M NaOH (10.5 mL; 21 mmol). The resulting deep blue reaction mixture was allowed to stir at 0° C. for 1.5 hours and was then blended into a vigorously agitated mixture of saturated aqueous $NH_4Cl$ (500 mL) and ethyl acetate (300 mL). The phases were separated and the aqueous phase was extracted once with ethyl acetate (100 mL), then the combined ethyl acetate layers were washed once with saturated aqueous $NH_4Cl$ (200 mL). The resulting ethyl acetate solution of (23) was then washed twice with a solution of $Na_2S_2O_4$ (25 g) in $H_2O$ (250 mL). The combined aqueous washes were extracted once with ethyl acetate (50 mL) then the combined ethyl acetate layers were washed once with saturated aqueous NaCl (brine) (150 mL), dried over $Na_2SO_4$, filtered and freed of solvent in vacuo to obtain a crude form of (24) as a brown tar which was used without purification. A solution of the crude (24) in methanol (10 mL) was slowly blended into rapidly stirring, deoxygenated (by inert gas purge) aqueous 2M HCl (250 mL) at ambient temperature. The resulting suspension was heated in a 100° C. oil bath under an inert gas atmosphere for 1.25 hours during which time a dark, gummy solid separated. The reaction mixture was cooled to ambient temperature, stirred rapidly with ethyl acetate (200 mL) and the phases separated; the aqueus layer was extracted once with ethyl acetate (200 mL) and then the combined ethyl acetate layers were washed once with brine (50 mL). The resulting ethyl acetate solution of (25) was oxidized by stirring vigorously for 15 minutes with a solution of $NaIO_4$ (3 g) in $H_2O$ (100 mL), then the phases were separated and the ethyl acetate layer was washed once with brine (100 mL), dried over $Na_2SO_4$, filtered and evaporated to dryness in vacuo to obtain a crude form of 7-hydroxy-1,3-dichloro-9,9-dimethyl-9H-acridin-2-one (26 which was then taken up in boiling ethyl alcohol (500 mL) and concentrated by boiling to a volume of ca. 150 mL. Upon cooling, the compound (26) separated in the form of fine ruddy-black needles to obtain, after two crops, 2.5 g (82%). A portion of the first crop was recrystallized from ethyl alcohol to obtain an analytical sample of (26) having no mp <250° C.

IR(KBr) $cm^{-1}$ 1624, 1492, 1451, 1304, 985, 500; $^1H$ NMR (DMSO-$d^6$) δ 1.74 (s, 6H), 6.84 (d of d, $J_1$=8.5 Hz and $J_2$=2.4 Hz, 1H), 7.06 (d, J=2.4 Hz, 1H), 7.50 (d, J=8.5 Hz, 1H), 7.76 (s, 1H); $^{13}C$ NMR (DMSO-$d^6$) ppm 172.07, 162,70, 145.73, 141.18, 140,85, 139.23, 134.8, 134.6, 134.28, 132.46, 115.95, 114.12, 26.27 (1 coincident band, one hidden by solvent bands);

Anal. Calcd. for $C_{15}H_{11}Cl_2NO_2$: C, 58.46; H, 3.60; N, 4.55. Found: C, 58.71; H, 3.83; N, 4.34.

(b) Synthesis of 7-Hydroxy-9,9-dimethyl-9H-acridin-2-one (20)

A solution of the dichloro compound (26) from step (a) of the present example (2.0 g; 6.49 mmol) in aqueous 1M NaOH (60 mL) and ethyl alcohol (40 mL) was treated with Raney Nickel 2800 (W. R. Grace and Co., Baltimore, Md., U.S.A.) (1 teaspoon) and hydrogenated at 40 psi $H_2$ with agitation at ca. 70° C. for 5 hours. After cooling to ambient temperature, the reaction mixture was filtered through diatomaceous earth (Celite ®, Johns-Manville Corp. Denver, Col., U.S.A.), diluted with $H_2O$ (500 mL) then acidified with aqueous 2M HCl (100 mL) and extracted five times with ethyl acetate (200 mL @). The combined ethyl acetate extracts were vigorously stirred with a solution of $NaIO_4$ (4 g) in $H_2O$ (300 mL) for 10 minutes at ambient temperature then treated with aqueous 1M HCl (100 mL). The phases were separated and the aqueous layer was washed twice with ethyl acetate (50 mL each); the combined ethyl acetate layers were washed once with brine (50 mL), dried over $MgSO_4$, filtered and evaporated to dryness in vacuo. Traces of residual water were removed by azeotroping with toluene and then vacuum drying at 60° C. to obtain the dimethyl chromogen (20) (1.38 g; 89%) in the form of a red powder. Recrystallization from ethyl acetate/hexane (1:1) afforded the dimethyl chromogen (20) in the form of ruby-red needles identical to that prepared by the method of Hill, et al., supra.

EXAMPLE 3

Synthesis of 7-β-D-Galactopyranosyloxy-9,9-dimethyl-9H-acridin-2-one (32) Employing 7-(Tetra-O-acetyl-β-D-galactopyranosyloxy-9,9-thyl-9H-acridin-2-one (31) Intermediate.

(a) Synthesis of 7-(Tetra-O-acetyl-β-D-galactopyranosyloxy)-9,9-dimethyl-9H-acridin-2-one (31)

A mixture of the dimethyl chromogen (20) prepared according to Example 2 (1.57 g; 6.56 mmol), acetobromogalactose (Sigma Chemical Co., St. Louis, Mo., U.S.A.) (3.238 g; 7.87 mmol), $Ag_2O$ (1.825 g; 7.87 mmol) and $CaSO_4$ (Drierite ®, W. A. Hammond Drierite Co. Xenia, Ohio U.S.A.) (2.625 g) in ethyl acetate (31.65 mL) containing anhydrous quinoline (15.8 mL) was stirred for 19 hours at ambient temperature in a stoppered flask protected from light. The reaction mixture was diluted with ethyl acetate (75 mL), filtered through Celite ® and extracted twice with aqueous 1.25 M HCl (75 mL each). The combined aqueous extracts were washed once with ethyl acetate (50 mL) then the combined ethyl acetate layers were washed twice with brine (35 mL each), thrice with 5% aqueous $NaHCO_3$ (75 mL each) and finally with brine (75 mL). The ethyl acetate solution was then dried over $Na_2SO_4$, filtered and evaporated to dryness in vacuo to result in a brownish-orange foam residue (4.78 g). The foam residue was taken up in ethyl acetate/hexane (3:2, 55 mL), treated with activated carbon (Darco ® G-60, ICI Americas, Inc. Wilmington, Del., U.S.A.) (4.78 g), and stirred at ambient temperature for 1 hour. The mixture was filtered through Celite ®, the filter cake was washed with ethyl acetate/hexane (3:2, 115 mL), then the filtrate and wash were combined and evaporated to dryness in vacuo to obtain a brownish-gold foam (4.17 g). The foam was taken up in boiling ethyl acetate (5.5 mL), diluted with hexane (9 mL) and vigorously scratched to induce crystallization to result in a yield of 3.0 g (80%) or 7-(tetra-O-acetyl-β-D-galactopyranosyloxy)-9,9-dimethyl-9H-acridin-2-one (31) after two crops. One recrystallization from ethyl acetate/hexane (2:1) resulted in an analytical sample of (31) in the form of rosettes of fine yellow needles having a melting point of 156.5°–158.0° C.

IR (KBr) cm$^{-1}$ 2970, 1755, 1645, 1620, 1515, 1375, 1235, 1080;

$^1$H NMR (DMSO-d$^6$) δ 1.50 (s, 6H), 1.93 (s, 3H), 1.97 (s, 3H), 1.97 (s, 3H), 2.01 (s 3H), 2.12 (s, 3H), 4.00–4.15 (m, 2H), 4.42–4.62 (m, 1H), 5.20–5.40 (m, 3H), 5.67–5.80 (m, 1H), 6.52–7.70 (m, 6H);

$^{13}$C NMR (DMSO-d$^6$) ppm 186.44, 169.92, 169.53, 169.20, 158.15, 151.00, 147.29, 141.44, 139.62, 137.34, 133.05, 131.23, 127.46 115.55, 113.80, 96.76, 70.75, 70.23, 68.28, 67.50, 61.84, 36.87, 32.25, 31.80, 20.42 (4 coincident bands);

Anal. Calcd. for $C_{29}H_{31}NO_{11}$: C 61.15; H, 5.49; N, 2.46. Found: C, 60.96; H, 5.54; N, 2.46

(b) Synthesis of 7-β-D-Galactopyranosyloxy-9,9-dimethyl-9H-acridin-2-one (32)

A solution of 7-(tetra-O-acetyl-β-D-galactopyranosyloxy)-9,9-dimethyl-9H-acridin-2-one (31) from step (a) of the present example (5.3 g; 9.3 mmol) in warm HPLC-grade methanol (250 mL) was cooled to ambient temperature and treated with sodium methoxide (0.106 g; 1.96 mmol). The hydrolysis reaction was followed by thin layer chromatography (silica gel; methanol/CHCl$_3$ (15:85)) and was complete after 1.33 hours. The reaction was quenched by addition of acetic acid (0.112 mL) and then evaporated to dryness in vacuo result in a dark, orange solid. The dark, orange solid was taken up in hot ethanol (75 mL), treated with Darco® G-60, stirred for 10 minutes, and then filtered through Celite® using warm ethanol (100 mL) to rinse the filter cake. The filtrate and wash were combined and concentrated in vacuo until the product began to separate, then the solution was further concentrated by boiling to a volume of ca. 50 mL. Upon cooling, the galactoside (32) separated as an amorphous orange powder and after two crops resulted in a yield of 3.3 g (88%). A portion was recrystallized from ethanol and vacuum dried (0.1 torr) at 132° C. for 1 hour to obtain an analytical sample of the galactoside (32) which appeared to scinter at ca. 140° C. before exhibiting a melting point of 184°–186° (decomposition point).

IR (KBR) cm$^{-1}$ 3400, 1635, 1610, 1505, 1240, 1070;

$^1$H NMR (DMSO-d$^6$) δ 1.50 (s, 6H), 3.40–3.72 (m, 6H), 4.51 (d, J=4.1 Hz, 1H), 4.66 [t, J=5.1 Hz, 1H), 4.88 (d, J=3.5 Hz, 1H), 5.00 (d, J7.7 Hz, 1H), 5.18 (d, J=5.0 Hz, 1H), 6.60 (d of d, J$_1$=9.8 Hz and J$_2$=2.0 Hz, 1H), 6.79 (d, J=2.0 Hz, 1H), 7.06 (d of d, J$_1$=8.7 Hz and J$_2$=2.6 Hz, 1H), 7.31 (d, J=2.6 Hz, 1H), 7.42 (d, J=9.8 Hz, 1H), 7.59 (d, J=8.7 Hz, 1H);

$^{13}$C NMR (DMSO-d$^6$) ppm 186.45, 159.60, 150.34, 147.52, 141.48, 139.51, 136.68, 133.00, 130.99, 127.26, 115.43, 114.10, 100.40, 75.79, 73.40, 70.22, 68.25, 60.48, 37.15, 32.28, 31.89;

Anal. Calcd. for $C_{21}H_{23}NO_7$: C,62.83;H, 5.78; N, 3.49. Found: C, 62.47; H, 5.73; N, 3.20.

EXAMPLE 4

Synthesis of 7-β-D-Glucopyranosyloxy-9,9-dimethyl-9H-acridin-2-one (34) Employing 7-(Tetra-O-acetyl-β-D-glucopyranosyloxy)-9,9-dimethyl-9H-acridin-2-one (33) Intermediate.

(a) Synthesis of 7-(Tetra-O-acetyl-β-D-glucopyranosyloxy)-9,9-dimethyl-9H-acridin-2-one (33)

A mixture of the dimethyl chromogen (20) prepared according to Example 2 (0.2393 g; 1.0 mmol), acetobromoglucose (Sigma Chemical Co., St. Louis, Mo., U.S.A.) (0.8224 g; 2.0 mmol) and Ag$_2$O (0.51 g; 2.2 mmol) was stirred in anhydrous quinoline (7.5 mL) for 17 hours at ambient temperature in a stoppered flask protected from light. The reaction mixture was diluted with ethyl acetate (100 mL), filtered through Celite® and twice extracted with aqueous 1.25 M HCl (50 mL each). The combined aqueous extracts were washed once with ethyl acetate (10 mL) then the combined ethyl acetate layers were washed once with brine (20 mL), once with 5% aqueous NaHCO$_3$ (50 mL) and once again with brine (20 mL). The ethyl acetate solution was then dried over Na$_2$SO$_4$, filtered and evaporated to dryness in vacuo. The crude product was chromatographed on silica gel (75 g) using acetone/CHCl$_3$ (1:9) solvent; the bright yellow major product band was collected and evaporated to dryness in vacuo to give an orange foam. The foam was crystallized from ethyl acetate/hexane (1:1) to afford 7-(tetra-O-acetyl-β-D-glucopyranosyloxy)-9,9dimethyl-9H-acridin-2-one (33) (0.498 g; 87%) in the form of golden-yellow tiny needles. A portion was recrystallized as above to obtain an analytical sample of (33) having a melting point of 142.0°–143.5° C.

IR (KBr) cm$^{-1}$ 2980, 1754, 1637, 1617, 1514, 1368, 1132, 1074, 1038; $^1$H NMR (DMSO-d$^6$) δ 1.52 (s, 6H), 1.91 (s, 3H), 1.99 (s, 3H), 2.01 (s, 3H), 2.02 (s, 3H), 3.98–4.19 (m, 2H), 4.32–4.38 (m, 1H), 5.03–5.13 (m, 2H), 5.42 (t, J=9.6 Hz, 1H), 5.83 (d, J=8.0 Hz, 1H), 6.62 (d of d, J$_1$=9.8 Hz and J$_2$2.1 Hz, 1H), 6.81 (d, J=2.1 Hz, 1H), 7.04 (d of d, J$_1$=8.7 Hz and J$_2$=2.7 Hz, 1H), 7.27 (d, J=2.7 Hz, 1H), 7.43 (d, J=9.8 Hz, 1H), 7.63 (d, J=8.7 Hz, 1H); $^{13}$C NMR (DMSO-d$^6$) ppm 186.46, 170.00, 169.62, 169.33, 169.12, 158.08, 150.99, 147.31, 141.44, 139.67, 137.32, 133.04, 131.26 127.47, 115.44, 113.84, 96.15, 72.03, 71.13, 70.58,68.96, 61.92, 37.13, 32.27, 31.79, 20.52, 20.40, 20.30 (one coincident peak);

Anal. Calcd. for $C_{29}H_{31}NO_{11}$:C, 61.15; H, 5.49; N 2.46. Found: C, 61 35; H, 5.58; N, 2.24.

(b) Synthesis of 7-β-D-Glucopyranosyloxy-9,9-dimethyl-9H-acridin-2-one (34)

A solution of 7-(tetra-O-acetyl-β-D-glucopyranosyloxy)-9,9-dimethyl-9H-acridin-2-one (×) from step (a) of the present example (0.47 g; 0.82 mmol) in HPLC-grade methanol (30 mL) was cooled in an ice bath, treated with sodium methoxide (20 mg) and allowed to warm to ambient temperature. The hydrolysis reaction was followed by thin layer chromatography (silica gel; methanol/CHCl$_3$ (15:85)) and was complete in 1.5 hours. The reaction was quenched by addition of acetic acid (ca. 20 μL) and evaporated to dryness in vacuo to give a crude form of the glucoside (34) as an orange foam. The crude form of the glucoside (34) was chromatographed on silica gel (75 g) using methanol/CHCl₃ (15:85) solvent and the major yellow product band was collected and freed of solvent in vacuo to result in an orange foam that was crystallized from a minimum volume of hot ethanol to obtain the glucoside (34) (0.28 g, 86%) in the form of bright orange tiny needles having a melting point of 232°–233° C. (dec.).

IR (KBr) cm$^{-1}$ 3320, 2900, 1627, 1604, 1500, 1230, 1083; $^1$H NMR (DMSO-d$^6$) δ 1.52 (s, 6H), 3.12–3.19 (m, 1H), 3.23–3.35 (m, 2H), 3.40–3.49 (m, 2H), 3.67–3.72 (m, 1H), 4.59 (t, J=5.2 Hz, 1H), 5.05 (d, J=6.2 Hz, 1H), 5.12 (d, J=4.0 Hz, 1H), 5.35 (d, J=4.4 Hz, 1H), 6.60 (d of d, J1=9.8 Hz and J2=2.1 Hz, 1H), 6.80 (d, J=2.0 Hz, 1H), 7.05 (d of d, J$_1$=8.7 Hz and J$_2$=2.6 Hz, 1H), 7.30 (d, J=2.5 Hz, 1H), 7.43 (d, J=9.8 Hz, 1H) 7.59 (d, J=8.7 Hz, 1H); $^{13}$C NMR (DMSO-d$^6$) ppm 186.15, 159.40, 150.28, 147.40, 141.26, 139.33, 136.65, 132.80, 130.82, 127.00, 115.37, 113.90, 99.90, 77.13, 76.64, 73.16, 69.66, 60.74, 37.00, 31.98. 31.65;

Anal. Calcd. for C$_{21}$H$_{23}$NO$_7$: C,62.83; H, 5.78; N, 3.49. Found: C, 62.49; H, 5.78; N, 3.64.

EXAMPLE 5

Synthesis of 7-(N-Tosyl-L-alaninyloxy)-9,9-dimethyl-9H-acridin-2-one (36) Employing N-Tosyl-L-Alaninyl Chloride Intermediate (35).

(a) Synthesis of N-Tosyl-L-Alaninyl Chloride (35)

The synthesis of N-tosyl-L-alaninyl chloride (35) employs, as a starting material, N-tosyl-L-alanine which was prepared according to the method described by Beecham, *J. Am. Chem. Soc.*, Vol. 79, p. 3257(1957). L-Alanine (Sigma Chemical Co., St. Louis, Mo., U.S.A.) (100 g; 1.11 moles) was dissolved in aqueous 1.0 M NaOH (2.25L), cooled to 5° C. and stirred while a solution of p-toluenesulfonyl chloride (tosyl chloride) (218 g; 1.11 moles) in toluene (450 mL) was added slowly. The mixture was stirred at ambient temperature for 20 hours. The layers were separated and the chilled aqueous layer was acidified to pH 1.0 with concentrated hydrochloric acid. The white solid was collected by filtration, washed with water and dried to obtain N-tosyl-L-alanine (178.5 g; 66%) having a melting point of 134°–135° C.

IR (CHCl₃) cm$^{-1}$ 1726, 1340, 1165, 1095; $^1$H NMR (DMSO-d$^6$) δ 1.20 (d, J=7 Hz, 3H), 2.40 (s, 3H), 3.85 (p, J=8 Hz, 1H), 6.4 (br. d, 1H), 7.41 (d, |J$_{AB}$|=8 Hz, 2H) and 7.75 (d,|J$_{AB}$|=8 Hz, 2H) (center of pattern: 7.58), 8.03 (br. d, J=8 Hz, 1H). N-Tosyl-L-alaninyl chloride (35) was then prepared according to methods (i) and (ii) below, employing N-tosyl-L-alanine, as follows:

(i) A mixture of N-tosyl-L-alanine (22.4 g; 0.05 mol) and thionyl chl[ride (25 mL) was heated for 1.5 hours at 55° C. and then evaporated to dryness in vacuo from a 40° C. bath. The red solid residue was dissolved in boiling CCl₄ (200 mL), decolorized with activated carbon (Norit® 211, American Norit Co., Inc., Jacksonville, Fla., U.S.A.), filtered and chilled. The cream colored, solid was collected by filtration, washed with hexane and dried to obtain N-tosyl-L-alaninyl chloride (35) (8.48 g; 65%) having a melting point of 101°–101.5° C.

IR (CHCl₃) cm$^{-1}$ 3360, 3260, 3025, 1775, 1605, 1350 1170, 910;

$^1$H NMR (CDCl₃) δ 1.48 (d, J=7 Hz, 3H), 2.43 (s, 3H), 4.33 (p, J=8 Hz, 1H), 5993 (br. d, J=8 Hz, 1H), 7.31 (d, |J$_{AB}$|=8 Hz, 2H) and 7.76 (d, |J$_{AB}$|=8 Hz, 2H) (center of pattern: 7.53).

Anal. Calcd. for C$_{10}$H$_{12}$ClNO$_3$S: C, 45.89; H, 4.62; N, 5.35. Found: C, 46,63; H, 4.90;N, 5.19.

(ii) A mixture of N-tosyl-L-alanine (3.1 g; 13 mmol) and thionyl chloride (6 mL) was heated for 1.5 hours at 50° C. then diluted with dry hexane (50 mmL). The mixture was stirred rapidly, chilled and the solid was collected by filtration to obtain 3.15 g (93%) of N-tosyl-L-alaninyl chloride (35) having a melting point of 99°–100° C. The IR spectrum of this material was identical to that of the recrystallized material prepared according to method (i).

(b) Synthesis of 7-(N-Tosyl-L-alaninyloxy)-9,9-dimethyl-9H-acridin-2-one (36).

A solution of the dimethyl chromogen (20) prepared according to Example 2 (38 mg; 0.16 mmol) in anhydrous tetrahydrofuran (3.2 mL) was stirred at ambient temperature and treated portionwise, over 1.5 hours, with N-tosyl-L-alaninyl chloride (35) from step (a) of the present example (243 mg; 0.93 mmol) and anhydrous pyridine (280 μL) while maintaining an inert gas atmosphere over the reaction. Once the addition was complete, the reaction was stirred for an additional hour then blended into ethyl acetate (50 mL) and then extracted twice with aqueous 1 N citric acid (10 mL @). The combined aqueous extracts were washed once with ethyl acetate (10 mL) and the combined ethyl acetate layers were extracted thrice with 5% aqueous NaHCO₃ (10 mL each). The combined NaHCO₃ extracts were washed once with ethyl acetate (10 mL) then the combined ethyl acetate layers were washed once with brine (20 mL), dried over Na₂SO₄, filtered and evaporated to dryness in vacuo to give an orange viscous oil (110 mg). This was chromatographed on silica gel (50 g) using acetone/CHCl₃ (9) solvent. The yellow major product band (R$_f$=0.32) was collected and evaporated to dryness in vacuo to obtain 7-(N-tosyl-L-alaninyloxy)-9,9-dimethyl-9H-acridin-2-one (36) (40 mg; 54%) in the form of a yellow glass.

IR (CHCL₃) cm$^{31}$ $^1$ 1758, 1639, 1617, 1516, 1343, 1215, 1165, 670;

$^1$H NMR (CDCl₃) δ1.52 (s, 6H), 1.57 (d, J=7.2 Hz, 3H), 2.44 (s, 3H), 4.22–4.32 (m, 1H), 5.25 (br. d, J=8.8 Hz, 1H), 6.65–6.59 (m, 2H), 6.86 (d of d, J$_1$=8.6 Hz and J$_2$=2.5 Hz, 1H), 7.07 (d, J=2.5 Hz, 1H), 7.40 (d, J=10.2 Hz, 1H), 7.33 (d, |J$_{AB}$|=8.1 Hz, 2H) and 7.81 (d, |J$_{AB}$|=8.1 Hz, 2H) (center of pattern: 7.57), 7.65 (d, J=8.6 Hz, 1H);

$^{13}$C NMR (CDCl₃) ppm 186.91, 170.58, 153.01, 151.66, 146.98, 143.87, 141.60, 140.16, 138.76, 137.13, 132.89, 132.04, 129.81, 127.97, 127.35, 120.62, 118.38, 51.76, 37.26, 32.14, 21.53, 19.58 (3 coincident bands).

EXAMPLE 6

Synthesis of Disodium-9,9-dimethyl-9H-acridin-2-one7-phosphate (37)

A solution of the dimethyl chromogen (20) prepared according to Example 2 (0.2393 g; 1.0 mmol) in anhydrous pyridine (3 mL) was maintained under an inert gas atmosphere, cooled to 0° C. and then treated in one portion with POCl₃ (0.28 mL; 3 mmol) and allowed to stir at 0° C. for 1 hour. The reaction mixture was blended into ambient temperature H₂O (100 mL) and the pH of the resulting solution was adjusted to 7.0 by careful addition of aqueous 10.0 M NaOH. The solution was concentrated in vacuo to a few mL and then chromatographed on silica gel (100 g) using ethanol/aqueous 1.0 M triethylammonium bicarbonate (7:3) solvent. The major yellow product band ($R_f$ in this system is ca. 0.45) was collected and evaporated to dryness in vacuo, then the residue was thrice dissolved in methanol (5 mL) and evaporated to dryness in vacuo to remove traces of triethylammonium bicarbonate. The residue was taken up in $H_2O$ (2–3 mL), passed through an ion exchange resin (Amberlite® IRC-50, Na-form, Rohm and Haas Co., Philadelphia, Pa., U.S.A.) column and the eluate evaporated to dryness in vacuo. The residue was triturated with methanol then the triturate was filtered through Celite® and evaporated to dryness in vacuo to result in a crude form of the disodium-acridinone-phosphate (37). The crude product (37) was taken up in a minimum of hot $H_2O$ (1–2 mL), diluted with a three-fold volume of ethanol and scratched to induce crystallization to obtain, after two crops, 0.0915 g (25%) of (37). A recrystallization from $H_2O$ ethanol (1:3) afforded an analytical sample of the disodium-acridinone-phosphate (37) in the form of fine brownish-orange needles which decomposed on heating above 100° C.

IR(KBr) $cm^{-1}$ 3430, 1635, 1610, 1505, 1246, 1124, 988, 953, 879, 711, 571; $^1H$ NMR ($D_2O$) δ1.57 (s, 6H), 6.72 (d of d, $J_1=9.8$ Hz and $J_2=2.1$ Hz, 1H), 6.86 (d, $J=2.2$ Hz, 1H), 7.28 (br. d of d, $J_1=8.3$ Hz and $J_2=2.0$ Hz, 1H), 7.50 (d, $J=9.8$ Hz, 1H), 7.53 (br. d, $J=2.4$ Hz, 1H), 7.63 (d, $J=8.7$ Hz, 1H); $^{13}C$ NMR ($D_2O$) ppm 192.16, 160.73, 153.18, 152.94, 144.60, 143.40, 139.05, 135.47, 133.47, 129.66, 122.43, 120.73, 40.46, 34.09 (1 coincident band).

EXAMPLE 7

Analytical Test Device for the Detection of β-D-Galactosidase

A 2 inch wide×2 inch long sheet of Whatman 54 filter paper (Whatman, Inc., Clifton, N.J., U.S.A.) was immersed in an aqueous solution comprising 0.3M bicine buffer (pH 7.9) and 4.0 mM $MgCl_2$ and air-dried overnight at room temperature. The filter paper was then immersed in a methanol solution containing 15 mM of the substrate product (32) from Example 3 and air-dried for one hour at room temperature to obtain a filter paper which was yellow in color.

A 0.5 cm wide×1.0 cm long segment of the above-described impregnated yellow filter paper was mounted onto and along the edge of one surface of a 0.5 cm×8.125 cm polystyrene support (Tricite®, Dow Chemical Co., Midland, Mich., U.S.A.) previously laminated with a 2 mm strip of Double Stick® double-faced adhesive tape (3M Company, St. Paul, Minn., U.S.A.) for use as an analytical test device for the detection of β-D-galactosidase from a liquid test sample.

EXAMPLE 8

Determination of β-D-Galactosidase From a Liquid Test Sample

Ten analytical test devices were prepared according to Example 4 and employed to determine the dose response of the substrate product compound (32) of the present invention to β-D-galactosidase.

Figure 4:
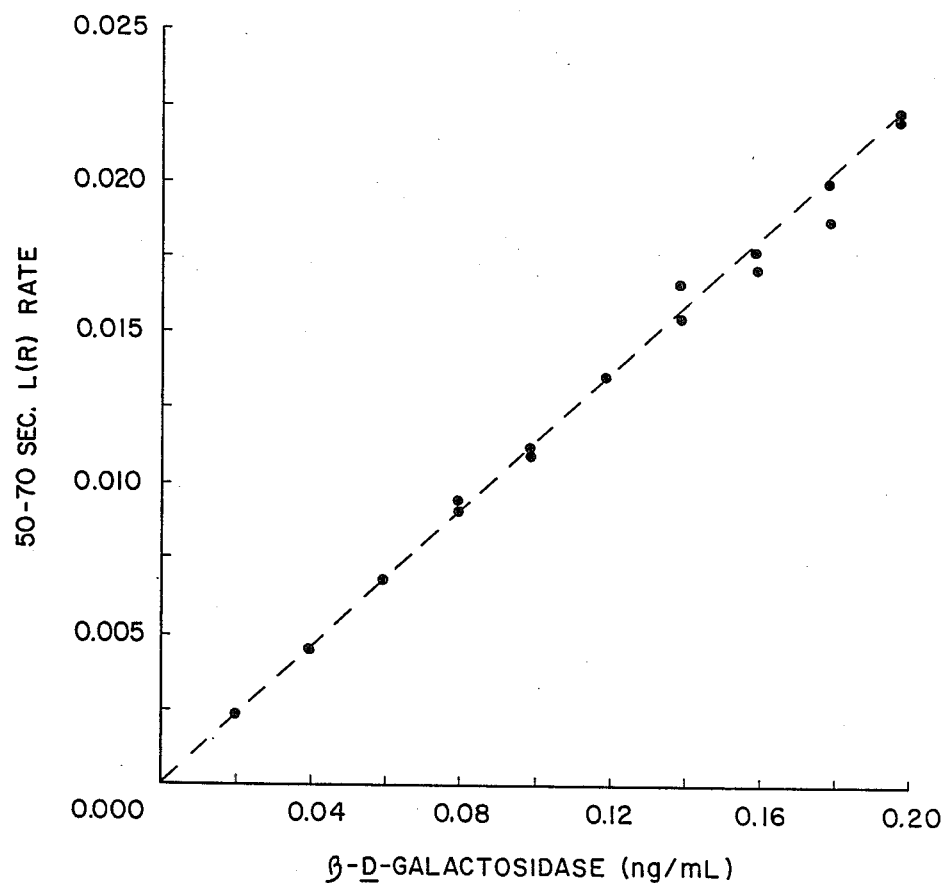
FIG. 4 is a graph which illustrates the dose response of a test device incorporated with the chromogenic enzyme substrate of the present invention to $\beta$-D-galactosidase.

Ten aqueous test sample solutions containing β-D-galactosidase concentrations of 0.02 ng/ml, 0.04 ng/ml, 0.06 ng/ml, 0.08 ng/ml, 0.12 ng/ml, 0.14 ng/ml, 0.16 ng/ml, 0.18 ng/ml and 0.20 ng/ml were prepared and an analytical test device dipped into each. The respective analytical test devices were then mounted in a SERALYZER® reflectance photometer (Miles Inc., Elkhart, Ind., U.S.A.) and the reflectance of light from the test device containing the liberated chromogen (20) as described in Example 1 was measured at 630 nm after 50–70 seconds, wherein the reflectance values thereof were plotted against the respective test sample solution concentrations to reveal a linear dose response as exemplified in FIG. 4.

EXAMPLE 9

Synthesis of 7-β-maltoheptaoslyxy-9,9-Dimethyl-acridin-2-one (43)/(DMA-G7)

A reaction mixture of 12.5 mM 7-β-D-glucopyranosyloxy-9,9-dimethyl-9H-acridin-2-one (34), hereinafter referred to as DMA-G1, from step (b) of Example 4, 62.0 mM α-cyclodextrin (Sigma Chemical Co., St. Louis, Mo., U.S.A.) and 56 units/mL of cyclodextrin glucanotransferase (EC 2.4.1.19, Ammano Pharmaceutical Co., Japan) in piperazine-N,N'-bis(2-ethanesulfonic acid) buffer (PIPES, pH 6.0) for 4 hours at 50° C. The mixture was then heated at 100° C. (boiling water) for 10 minutes to inactivate the cyclodextrin glucanotransferase, and then evaporated to dryness under a vacuum and redissolved in 0.5 mL water to result in a mixture of the glucoside (DMA-G1), unsubstituted maltooligosaccharides (e.g., glucose, maltose, maltotriose, maltotetrose, maltopentose, maltohexose, maltoheptose, and α-cyclodextrin), and the desired 7-β-maltoheptaosyloxy-9,9-dimethyl-acridin-2-one (DMA-G7) compound and shorter chain-length chromogenic maltooligosaccharides (7-β-malto, -maltotrio,-maltotetra, -maltopenta and -maltohexaosyloxy-9,9-dimethyl-acridin-2-ones, i.e., hereinafter referred to as DMA-G2 (38), DMA-G3 (39), DMA-G4 (40), DMA-G5 (41) and DMA-G6 (42), respectively) of the formula shown in Table 1.

The desired DMA-G7 species were separated from DMA-G1 to DMA-G6 species by high pressure liquid chromatography (HPLC) employing a preparative reversed-phase C-18 column (Regis Chemical Co., Morton Grove, Ill., U.S.A.). The system consisted of two Constametric-III metering pumps, Chromatography Control Module, and a Spectromonitor II detector (all from Laboratory Data Control, Riviera Beach, Fla., U.S.A.). The redissolved substrate reaction mixture was injected into the HPLC system and eluted for 90 minutes at a flow rate of 6.0 mL/minute. A linear gradient from 0% to 25% $CH_3CN/H_2O$ was employed for eluting the DMA-G1 to DMA-G7 and unsubstituted maltooligosaccharide species from the column. The unsubstituted maltooligosaccharides were eluted and removed at hhe void volume, and the column eluant was monitored at 520 nm to detect the fractions containing the DMA-G1 to DMA-G7 species. The fractions (9.0 mL) containing DMA-G7, DMA-G6, DMA-G5, DMA-G4, DMA-G3, DMA-G2 and DMA-G1 were collected at retention times of 42.5, 44.6, 48.5, 53.1, 58.5, 64.6 and 70.8 minutes respectively, with a fraction collector (LKB, Bromma, Sweden) whereby about 50% of the DMA-G1 from the reaction mixture was converted to the desired DMA-G7. The fraction containing the DMA-G7 collected at 42.5 minutes was reanalyzed by HPLC to assure its purity.

TABLE 1

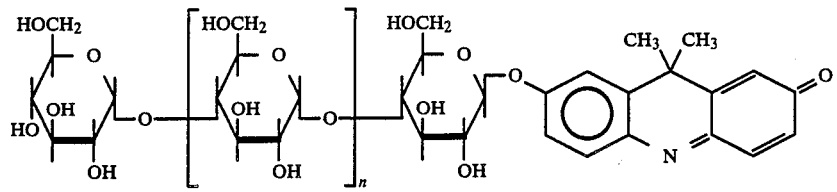

| Compound Number | n | Reference Symbol |
|---|---|---|
| 38 | 0 | DMA-G2 |
| 39 | 1 | DMA-G3 |
| 40 | 2 | DMA-G4 |
| 41 | 3 | DMA-G5 |
| 42 | 4 | DMA-G6 |
| 43 | 5 | DMA-G7 |

EXAMPLE 10

Liquid Analytical Test System for the Detection of α-Amylase

A liquid α-amylase detection reagent was prepared by combining 1.8 mM DMA-G7 (43) prepared according to Example 9, 38 units of α-glucosidase and 20 units of β-glucosidase in 1.0 mL of buffered solution comprising 50 mM PIPES, 50 mM NaCl, and 5.0 mM calcium chloride (pH 7.0). Amylase control serum (0.025 mL) containing 37 IU/L, 175 IU/L, and 313 IU/L, respectively, of α-amylase were added to the detection reagent, independently, and incubated at 37° C. The enzymatic action of α-amylase on the substrate compound in each of the mixtures liberated shorter chain chromogenic maltooligosaccharide compounds thereof (e.g., DMA-G2 to DMA-G4) which, in turn, was enzymatically acted upon by the α-glucosidase and β-glucosidase to liberate the optically active form of the dimethyl acridinone chromogen (20). The rate of color change produced by the liberated chromogen in each of the mixtures was measured at 634 nm on a Cary 219 spectrophotometer (Varian Associates, Inc., Sonnyvale, Calif., U.S.A.) from between 1 and 9 minutes after each of the serum samples were added to the detection reagent (Table 2). The α-amylase reactivities in the samples were calculated by taking an average of three consecutive readings between 3 and 6 minutes and a linear dose response to the α-amylase concentration was derived therefrom (Table 3).

TABLE 2

| Time (minutes) | Absorbance (634 nm) | | |
|---|---|---|---|
|  | 37 IU/L | 175 IU/L | 313 IU/L |
| 1 | 0.123 | 0.150 | 0.171 |
| 2 | 0.129 | 0.178 | 0.212 |
| 3 | 0.138 | 0.223 | 0.282 |
| 4 | 0.148 | 0.279 | 0.372 |
| 5 | 0.160 | 0.341 | 0.474 |
| 6 | 0.172 | 0.409 | 0.585 |
| 7 | 0.187 | 0.481 | 0.702 |
| 8 | 0.202 | 0.555 | 0.823 |
| 9 | 0.218 | 0.631 | 0.948 |

TABLE 3

| Amylase (IU/L) | Absorbance/Minute |
|---|---|
| 37 | 0.011 |
| 175 | 0.062 |
| 313 | 0.109 |

EXAMPLE 11

Analytical Test Device for the Detection of α-Amylase

A sheet of Whatman 54 filter paper (Whatman, Inc., Clifton, N.J., U.S.A.) was immersed into a solution comprising the liquid α-amylase detection reagent prepared according to Example 10, 0.1% Triton X-100 (Sigma Chemical Co., St. Louis, Mo., U.S.A.) and 0.5% carboxycellulose, and dried.

Analytical test devices were prepared by mounting 0.5 cm wide×1.0 cm long segment of the aforementioned impregnated filter paper onto and along the edge of one surface of 0.5 cm×8.125 cm polystyrene supports (Tricite ®, Dow Chemical Co., Midland, Mich., U.S.A.) previously laminated with a 2 mm strip of Double Stick ® double-faced adhesive tape (3M Company, St. Paul, Minn., U.S.A.).

Three 30 μL aliquots of undiluted serum containing 39 IU/L, 78 IU/L, 117 IU/L, 157 IU/L, 235 IU/L, and 313 IU/L, respectively, of α-amylase were applied, independently, to a test device and the rate of color change produced by the liberated chromogen on each device was measured at 630 nm on a Seralyzer ® reflectance photometer (Miles Inc., Elkhart, Ind., U.S.A.) from between 0 seconds and 240 seconds after the serum sample was added to each test device. In order to linearize the reflectance data generated by the rate of color change with respect to the concentration of α-amylase, the test device reactivities were determined by taking a linear regression of L(R) where L(R)=a/(R+b) and where R=reflectance, a=0.57986 and b=0.16498, between 180 and 200 seconds, and a linear dose response to α-amylase was derived therefrom (Table 4).

It will be apparent that many modifications and variations of the invention as herein set forth are possible without departing from the spirit and scope thereof, and that, accordingly, such limitations are imposed only as indicated by the appended claims.

TABLE 4

| Amylase (IU/L) | Reactivity × $10^{-2}$ |
|---|---|
| 39 | 0.384 |
|  | 0.373 |
|  | 0.359 |
| 78 | 0.957 |
|  | 0.941 |
|  | 0.954 |
| 117 | 1.450 |
|  | 1.510 |
|  | 1.430 |
| 157 | 1.781 |

TABLE 4-continued

| Amylase (IU/L) | Reactivity × 10⁻² |
| --- | --- |
|  | 1.999 |
|  | 1.886 |
| 235 | 2.560 |
|  | 2.596 |
|  | 2.610 |
| 313 | 2.961 |
|  | 2.989 |
|  | 2.916 |

What is claimed is:

1. A chromogenic enzyme substrate compound of the formula:

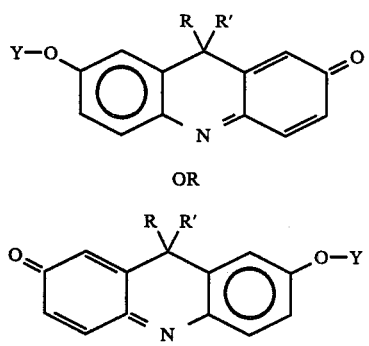

wherein Y represents an enzymatically-cleavable group and

R and R', which can be the same or different, are alkyl or aryl, or together form a cyclohexadienone or hydroxycyclohexyl residue.

2. The compound of claim 1 wherein said enzymatically-cleavable group is a radical of a compound Y—OH comprising an enzyme-specific moiety selected from the group consisting of sugars and derivatives thereof, aliphatic and aromatic carboxylic acids, and inorganic acids.

3. The compound of claim 2 wherein said enzyme-specific moiety is a sugar or derivative thereof selected from the group consisting of α-D-galactose, β-D-galactose, α-D-glucose, β-D-glucose, α-D-mannose, N-acetylglucosamine and N-acetylneuraminic acid.

4. The compound of claim 2 wherein said enzyme-specific moiety is an oligosaccharide chain of from between about 2 to 20 monosaccharide units.

5. The compound of claim 2 wherein said enzyme-specific moiety is an oligosaccharide selected from the group consisting of maltopentose, maltohexose and maltoheptose.

6. The compound of claim 2 wherein said enzyme-specific moiety is β-D-galactose.

7. The compound of claim 2 wherein said enzyme-specific moiety is β-D-glucose.

8. The compound of claim 2 wherein said enzyme-specific moiety is α-D-glucose.

9. The compound of claim 2 wherein said enzyme-specific moiety is maltoheptose.

10. The compound of claim 2 wherein said enzyme-specific moiety is an aliphatic or aromatic carboxylic acid.

11. The compound of claim 2 wherein said enzyme-specific moiety is a carboxylic acid comprising an N-protected amino acid or peptide of from between about 2 to 5 amino acid units.

12. The compound of claim 11 wherein said enzyme-specific moiety is N-tosyl-L-alanine.

13. The compound of claim 2 wherein said enzyme-specific moiety is phosphoric acid or sulfuric acid.

14. The compound of claim 13 wherein said enzyme-specific moiety is phosphoric acid.

15. The compound of claim 1 wherein R and R', which can be the same or different, are alkyl or phenyl or together form a cyclohexa-2,5-diene-4-one residue or a 4-hydroxycyclohexyl residue.

16. The compound of claim 1 wherein R and R', which can be the same or different, are alkyl or phenyl.

17. The compound of claim 1 wherein R and R', which can be the same or different, are lower alkyl comprising 6 or less carbons or phenyl.

18. A chromogenic enzyme substrate compound of the formula:

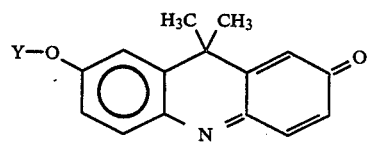

wherein Y is a radical of a compound Y—OH comprising an enzyme-specific moiety selected from the group consisting of sugars and derivatives thereof, aliphatic and aromatic carboxylic acids, and phosphoric acid.

19. The compound of claim 18 wherein said enzyme-specific moiety is a sugar or derivative thereof selected from the group consisting of α-D-galactose, β-D-galactose, α-glucose, β-glucose, α-mannose, N-acetylglucosamine and N-acetylneuraminic acid.

20. The compound of claim 18 wherein said enzyme-specific moiety is an oligosaccharide chain of from between about 2 to 20 monosaccharide units.

21. The compound of claim 18 wherein said enzyme-specific moiety is β-D-galactose.

22. The compound of claim 18 wherein said enzyme specific moiety is β-D-glucose.

23. The compound of claim 18 wherein said enzyme-specific moiety is α-D-glucose.

24. The compound of claim 18 wherein said enzyme-specific moiety is maltoheptose.

25. The compound of claim 18 wherein said enzyme-specific moiety is a carboxylic acid comprising an N-protected amino acid or peptide of from between about 2 to 5 amino acid units.

26. The compound of claim 25 wherein said enzyme-specific moiety is N-tosyl-L-alanine.

27. The compound of claim 18 wherein said enzyme-specific moiety is phosphoric acid.

28. A method for preparing chromogenic acridinone enzyme substrate compounds of the formula:

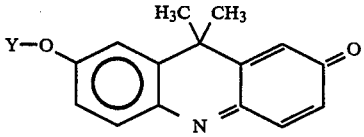

wherein Y is a radical of a compound Y—OH comprising an enzyme-specific sugar moiety, the method comprising the steps of:

(a) reacting an acridinone chromogen of the formula:

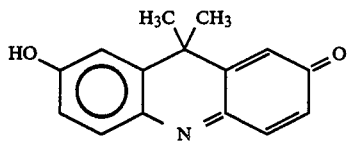

with a 1-halogeno-derivative of said enzyme-specific sugar moiety substituted, independently, at the hydroxy-positions thereof with protecting groups to result in a per-O-substituted derivative of said chromogenic acridinone enzyme substrate compound; and (b) reacting said per-O-substituted derivative with a hydrolyzing reagent to remove said protecting groups to obtain said chromogenic acridinone enzyme substrate compound.

29. The method of claim 28 wherein said 1-halogeno-derivative of said enzyme specific moiety is a 1-bromo-derivative and said protecting groups are acetate protecting groups.

30. The method of claim 29 wherein said enzyme-specific moiety is β-D-galactose.

31. The method of claim 29 wherein said enzyme-specific moiety is β-D-glucose.

32. A method for determining a particular enzyme in a liquid test sample comprising the steps of:

(a) contacting the test sample with a chromogenic acridinone enzyme substrate compound of the formula:

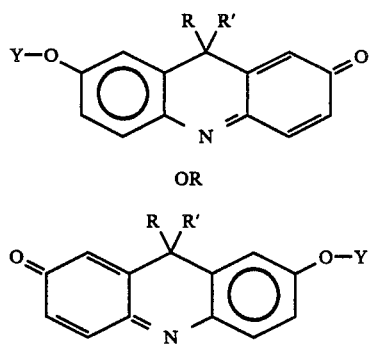

wherein R and R', which can be the same or different, are alkyl or aryl or together form a cyclohexadieneone or hydroxycyclohexyl residue, and Y is an enzymatically-cleavable group which is (i) capable of being cleaved from the acridinone indicator group by said enzyme or (ii) capable of being modified by said enzyme to be determined to produce a secondary substrate compound in which the enzymatically-cleavable group is cleavable from the acridinone indicator group by a secondary enzyme, in which case the secondary substrate compound is contacted with said secondary enzyme; and (b) measuring and correlating the resulting color generated by the cleaved acridinone indicator group to the amount of said enzyme present in said liquid test sample.

33. The method of claim 32 wherein said enzymatically-cleavable group is a radical of a compound Y—OH comprising an enzyme-specific moiety selected from the group consisting of sugars and derivatives thereof, aliphatic and aromatic carboxylic acids, phosphoric acid, and sulfuric acid.

34. The method of claim 33 wherein R and R', which can be the same or different, are alkyl or phenyl or together form a cyclohexa-2,5-diene-4-one residue or a 4-hydroxycyclohexyl residue.

35. The method of claim 33 wherein R and R', which can be the same or different, are alkyl or phenyl.

36. The method of claim 33 wherein R and R', which can be the same or different, are lower alkyl comprising 6 or less carbons or phenyl.

37. The method of claim 33 wherein R and R' are both methyl.

38. The method of claim 37 wherein said enzyme is a glycosidase and Y is a radical of a sugar or derivative thereof selected from the group consisting of α-D-galactose, β-D-galactose, α-D-glucose, β-D-glucose, α-D-mannose, N-acetylglucosamine and N-acetylneuraminic acid.

39. The method of claim 37 wherein said enzyme is α-amylase and Y is a radical of an oligosaccharide chain of from between 2 to 20 monosaccharide units which is capable of being modified by α-amylase to produce a secondary glycoside substrate compound in which the resulting glycoside group is cleavable from the acridinone indicator group by a secondary glycosidase enzyme, and wherein the secondary glycoside substrate compound is contacted with said secondary glycosidase enzyme.

40. The method of claim 39 wherein said oligosaccharide chain is maltoheptose.

41. The method of claim 39 wherein said resulting glycoside group is a glucoside and said secondary glycosidase enzyme is a glucosidase.

42. The method of claim 37 weerein said enzyme is β-D-galactosidase and Y is a β-D-galactose radical.

43. The method of claim 37 wherein said enzyme is β-D-glucosidase and Y is a β-D-glucose radical.

44. The method of claim 37 wherein said enzyme is a non-specific esterase and Y is a radical of an aliphatic or aromatic carboxylic acid.

45. The method of claim 37 weerein said enzyme is a proteolytic enzyme present in leukocytes and Y is a radical of a carboxylic acid comprising an N-protected amino acid or peptide of from between about 2 to 5 amino acid units.

46. The method of claim 44 wherein Y is an N-tosyl-L-alanine radical.

47. The method of claim 37 wherein said enzyme is alkaline phosphatase and Y is a phosphoric acid radical.

48. The method of claim 37 wherein said enzyme is sulfatase and Y is a sulfuric acid radical.

49. A test device for the determination of a particular enzyme in a liquid test sample, the test device comprising a carrier matrix incorporated with a chromogenic acridinone enzyme substrate compound of the formula:

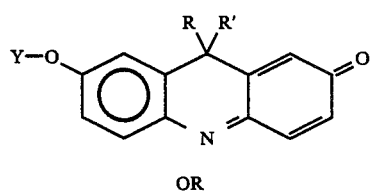

-continued

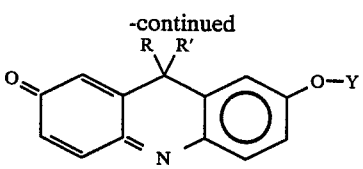

wherein R and R', which can be the same or different are alkyl or aryl or together form a cyclohexadieneone or hydroxycyclohexyl residue, and Y is an enzymatically-cleavable group which is (i) capable of being cleaved from the acridinone indicator group by said enzyme or (ii) capable of being modified by said enzyme to be determined to produce a secondary substrate compound in which the enzymatically-cleavable group is cleavable from the acridinone indicator group by a secondary enzyme, in which case said carrier matrix is also incorporated with said secondary enzyme.

50. The test device of claim 49 wherein said enzymatically-cleavable group is a radical of a compound Y—OH comprising an enzyme-specific moiety selected from the group consisting of sugars and derivatives thereof, aliphatic and aromatic carboxylic acids, phosphoric acid, and sulfuric acid.

51. The test device of claim 50 wherein R and R', which can be the same or different, are alkyl or phenyl or together form a cyclohexa-2,5-diene-4-one residue or a 4-hydroxycycloheyyl residue.

52. The test device of claim 50 wherein R and R', which can be the same or different, are alkyl or phenyl.

53. The test device of claim 50 wherein R and R', which can be the same or different, are lower alkyl comprising 6 or less carbon atoms or phenyl.

54. The test device of claim 50 wherein R and R' are both methyl.

55. The test device of claim 54 wherein said enzyme is a glycosidase and Y is a radical of a sugar or derivative thereof selected from the group consisting of α-D-galactose, β-D-galactose, α-D-glucose, β-D-glucose, α-mannose, N-acetylglucosamine and N-acetylneuraminic acid.

56. The test device of claim 54 wherein said enzyme is α-amylase and Y is a radical of an oligosaccharide chain of from between 2 to 20 monosaccharide units which is capable of being modified by α-amylase to produce a secondary glycoside substrate compound in which the resulting glycoside group is cleavable from the acridinone indicator group by a secondary glycosidase enzyme, said carrier matrix also being incorporated with said secondary glycosidase enzyme.

57. The test device of claim 56 wherein said oligosaccharide chain is maltoheptose.

58. The test device of claim 56 wherein said resulting glycoside group is a glucoside and said secondary glycosidase enzyme is a glucosidase.

59. The test device of claim 54 wherein said enzyme is β-D-galactosidase and Y is a β-D-galactose radical.

60. The test device of claim 54 wherein said enzyme is β-D-glucosidase and Y is a β-D-glucose radical.

61. The test device of claim 54 wherein said enzyme is a non-specific esterase and Y is a radical of an aliphatic or aromatic carboxylic acid.

62. The test device of claim 54 wherein said enzyme is a proteolytic enzyme present in leukocytes and Y is a radical of a carboxylic acid comprising an N-protected amino acid or peptide of between about 2 to 5 amino acid units.

63. The test device of claim 62 wherein Y is an N-tosyl-L alanine radical.

64. The test device of claim 54 wherein said enzyme is alkaline phosphatase and Y is a phosphoric acid radical.

65. The test device of claim 54 wherein said enzyme is sulfatase and Y is a sulfuric acid residue.

66. An acridinone chromogen of the tautomeric formula:

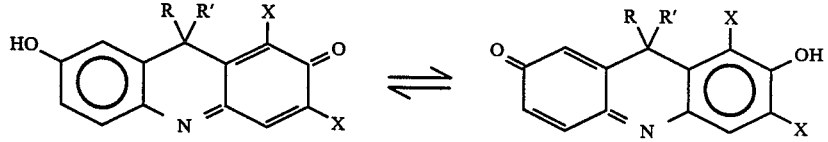

wherein R and R', which can be the same or different, are alkyl or aryl, and X is halo.

67. The chromogen of claim 66 wherein R and R', which can be the same or different, are lower alkyl comprising 6 or less or phenyl and X is bromo or chloro.

68. The chromogen of claim 67 wherein R and R' are methyl and X is chloro.

* * * * *